US011244246B2

(12) United States Patent
Farh et al.

(10) Patent No.: US 11,244,246 B2
(45) Date of Patent: Feb. 8, 2022

(54) FEDERATED SYSTEMS AND METHODS FOR MEDICAL DATA SHARING

(71) Applicant: ILLUMINA, INC., San Diego, CA (US)

(72) Inventors: Kai-How Farh, San Mateo, CA (US);
Donavan Cheng, Foster City, CA (US);
John Shon, Portola Valley, CA (US);
Jorg Hakenberg, Foster City, CA (US);
Eugene Bolotin, San Diego, CA (US);
James Casey Geaney, Oakland, CA (US); Hong Gao, San Diego, CA (US);
Pam Cheng, San Diego, CA (US);
Inderjit Singh, San Diego, CA (US);
Daniel Roche, San Diego, CA (US);
Milan Karangutkar, Santa Clara, CA (US)

(73) Assignee: ILLUMINA, INC., San Diego, CA (US)

( * ) Notice: Subject to any disclaimer, the term of this patent is extended or adjusted under 35 U.S.C. 154(b) by 104 days.

(21) Appl. No.: 16/799,071

(22) Filed: Feb. 24, 2020

(65) Prior Publication Data

US 2020/0380412 A1 Dec. 3, 2020

Related U.S. Application Data

(63) Continuation of application No. 15/683,714, filed on Aug. 22, 2017, now Pat. No. 10,607,156.
(Continued)

(51) Int. Cl.
*G06F 7/00* (2006.01)
*G06N 20/00* (2019.01)
(Continued)

(52) U.S. Cl.
CPC ........... *G06N 20/00* (2019.01); *G06F 16/248* (2019.01); *G06F 16/2471* (2019.01);
(Continued)

(58) Field of Classification Search
CPC .... G16H 70/60; G16H 80/00; G06F 16/2471; G06F 16/248
(Continued)

(56) References Cited

U.S. PATENT DOCUMENTS

2004/0122707 A1\* 6/2004 Sabol ....................... G07C 9/37
                                                                 705/2
2007/0150315 A1\* 6/2007 Bennett ............... G06F 21/6245
                                                                 705/3
(Continued)

FOREIGN PATENT DOCUMENTS

WO 2015089088 A1 6/2015
WO 2017/214046 A1 12/2017
WO 2018039276 A1 3/2018

OTHER PUBLICATIONS

Zhong, N., "Representation and Construction of Ontologies for Web Intelligence", International Journal of Foundations of Computer Science vol. 13 (4), 2002, 555-570.

*Primary Examiner* — Md I Uddin
(74) *Attorney, Agent, or Firm* — Fletcher Yoder, P.C.

(57) ABSTRACT

Systems, computer-implemented methods, and non-transitory computer readable media are provided for sharing medical data. The disclosed systems may be configured to create a first workgroup having a first knowledgebase. This first knowledgebase may be federated with a common knowledgebase, and with a second knowledgebase of a second workgroup. At least one of the first knowledgebase, common knowledgebase, and second knowledgebase may be configured to store data items comprising associations, signs, and evidence. The signs may comprise measurements
(Continued)

and contexts, and the associations may describe the relationships between the measurements and contexts. The evidence may support these associations. The disclosed systems may be configured to receive a request from a user in the first workgroup, retrieve matching data items, and optionally then output to the user at least some of the retrieved matching data items. The request may comprise at least one of a first association and a first measurement.

41 Claims, 12 Drawing Sheets

Related U.S. Application Data

(60) Provisional application No. 62/378,675, filed on Aug. 23, 2016.

(51) Int. Cl.
| | | |
|---|---|---|
| *G06F 16/248* | (2019.01) | |
| *G06F 16/2458* | (2019.01) | |
| *G06F 16/25* | (2019.01) | |
| *G16H 70/60* | (2018.01) | |
| *G06N 5/02* | (2006.01) | |
| *G06Q 50/00* | (2012.01) | |
| *G06N 5/04* | (2006.01) | |
| *H04L 29/08* | (2006.01) | |
| *G16H 80/00* | (2018.01) | |
| *G16H 10/60* | (2018.01) | |
| *H04L 29/06* | (2006.01) | |

(52) U.S. Cl.
CPC ........... *G06F 16/256* (2019.01); *G06N 5/022* (2013.01); *G06N 5/04* (2013.01); *G06Q 50/01* (2013.01); *G16H 70/60* (2018.01); *G16H 80/00* (2018.01); *H04L 67/306* (2013.01); *G16H 10/60* (2018.01); *H04L 67/10* (2013.01); *H04L 67/42* (2013.01)

(58) Field of Classification Search
USPC .......................... 707/722, 736, 737, 756, 769
See application file for complete search history.

(56) References Cited

U.S. PATENT DOCUMENTS

| | | |
|---|---|---|
| 2007/0214016 A1* | 9/2007 | Bennett ................. G06F 16/283 705/3 |
| 2009/0156906 A1 | 6/2009 | Liebman et al. |
| 2013/0006932 A1 | 1/2013 | Akulavenkatavara et al. |
| 2013/0291060 A1 | 10/2013 | Moore et al. |
| 2014/0046926 A1 | 2/2014 | Walton |
| 2015/0134262 A1 | 5/2015 | Downs et al. |
| 2018/0060523 A1 | 3/2018 | Farh et al. |

* cited by examiner

FEDERATED SYSTEMS AND METHODS FOR MEDICAL DATA SHARING

CROSS-REFERENCE TO RELATED APPLICATIONS

This application is a continuation of U.S. application Ser. No. 15/683,714, filed Aug. 22, 2017, which claims priority to U.S. Provisional Patent Application No. 62/378,675, filed Aug. 23, 2016, which is hereby incorporated by reference herein in its entirety.

TECHNICAL FIELD

The disclosed systems and methods generally concern computerized collaboration systems for sharing data using a federated system. More specifically, the disclosed systems and methods concern sharing medical data without risking disclosure of personally identifiable patient information.

SUMMARY

Medical providers may lack familiarity with rare medical conditions. For example, individual genetics laboratories often encounter rare genetic variants so infrequently that they fail to recognize the effects these variants may have on human health. The disclosed systems and methods enable collaborative sharing of medical data, without risking disclosure of personally identifiable patient information. By using the disclosed collaboration platform, medical providers may share expertise, and content providers may provide new or updated information about medical conditions.

The disclosed systems and methods may enable collaborative sharing of medical data. A computer system for sharing data can include: at least one processor; and at least one non-transitory memory. The at least one non-transitory memory can store instructions that, when executed by the at least one processor, can cause the system to perform operations including: creating a federated system comprising a common knowledgebase, a first workgroup having a first knowledgebase, and a second knowledgebase of a second workgroup. The federated system can include a data structure that is configured to store categories for signs, associations, and evidences of variant data. The operations can include storing data items in the federated system, the data items comprising the signs, associations, or evidence. The category for signs storing biomarker measurements and contexts of phenotypes, diseases or drugs, the category for associations storing an association between at least a biomarker measurement and a context, and the category for evidence storing information supporting the associations. The operations can include connecting the common knowledgebase, the first knowledgebase and the second knowledgebase through a federated layer, each of the knowledgebases that are connected participating in the federated system. The operations can include upon receiving a prompt from a user of one of the first or second workgroup to discontinue participation in the federated system, disconnecting the one of the first or the second workgroup from the other of the first or the second workgroup. The operations can include receiving a request from the user, the request comprising at least one of an association and a measurement. The operations can include performing a federated search, in real-time through the federated layer, for the received request from the user through the knowledgebases that are participating in the federated system, the federated search being performed without using personal information of patients of the first or second knowledgebase. The operations can include retrieving matching data items from the federated search of the at least one of the common knowledgebase, first knowledgebase, and second knowledgebase; and outputting to the user at least some of the retrieved matching data items.

A non-transitory computer-readable medium can store instructions that, when executed by at least one processor of a system, cause a first node of the system to perform operations comprising: creating a federated system comprising a common knowledgebase, a first workgroup having a first knowledgebase, and a second knowledgebase of a second workgroup. The federated system can include a data structure that is configured to store categories for signs, associations, and evidences of variant data. The operations can include storing data items in the federated system 117, the data items comprising the signs, associations, or evidence, the category for signs storing biomarker measurements and contexts of phenotypes, diseases or drugs, the category for associations storing an association between at least a biomarker measurement and a context, and the category for evidence storing information supporting the associations. The operations can include connecting the common knowledgebase, the first knowledgebase and the second knowledgebase through a federated layer, each of the knowledgebases that are connected participating in the federated system. The operations can include upon receiving a prompt from a user of one of the first or second workgroup to discontinue participation in the federated system, disconnecting the one of the first or the second workgroup from the other of the first or the second workgroup. The operations can include receiving a request from the user, the request comprising at least one of an association and a measurement. The operations can include performing a federated search, in real-time through the federated layer, for the received request from the user through the knowledgebases that are participating in the federated system, the federated search being performed without using personal information of patients of the first or second knowledgebase. The operations can include retrieving matching data items that satisfy the federated request from at least one of the first knowledgebase, common knowledgebase, and second knowledgebase; and outputting at least some of the associated retrieved matching data items to the user.

A computer-implemented method for sharing data can include: creating a federated system comprising a common knowledgebase, a first workgroup having a first knowledgebase, and a second knowledgebase of a second workgroup. The federated system can include a data structure that is configured to store categories for signs, associations, and evidences of variant data. The federated system can include a plurality of processors and a plurality of storage devices. The method can include storing data items in the storage devices of the federated system. The data items can include the signs, associations, or evidence. The category for signs can store biomarker measurements and contexts of phenotypes, diseases or drugs, the category for associations storing an association between at least a biomarker measurement and a context, and the category for evidence storing information supporting the associations. The method can include connecting the common knowledgebase, the first knowledgebase and the second knowledgebase through a federated layer, each of the knowledgebases that are connected participating in the federated system. The method can include upon receiving a prompt from a user of one of the first or second workgroup to discontinue participation in the federated system, disconnecting the one of the first or the second workgroup from the other of the first or the second workgroup. The method can include receiving a request from the user, the request comprising at least one of an association and a measurement. The method can include performing a federated search, in real-time through the federated layer, for the received request from the user through the knowledgebases that are participating in the federated system, the federated search being performed without using personal information of patients of the first or second knowledgebase. The method can include retrieving matching data items from the federated search of the at least one of the common knowledgebase, first knowledgebase, and second knowledgebase; and outputting to the user at least some of the retrieved matching data items.

It is to be understood that both the foregoing general description and the following detailed description are exemplary and explanatory only and are not restrictive of the disclosed embodiments, as claimed.

BRIEF DESCRIPTION OF THE DRAWINGS

The drawings are not necessarily to scale or exhaustive. Instead, emphasis is generally placed upon illustrating the principles of the inventions described herein. The accompanying drawings, which are incorporated in and constitute a part of this specification, illustrate several embodiments consistent with the disclosure and, together with the description, serve to explain the principles of the disclosure. In the drawings.

DETAILED DESCRIPTION

Figure 1:
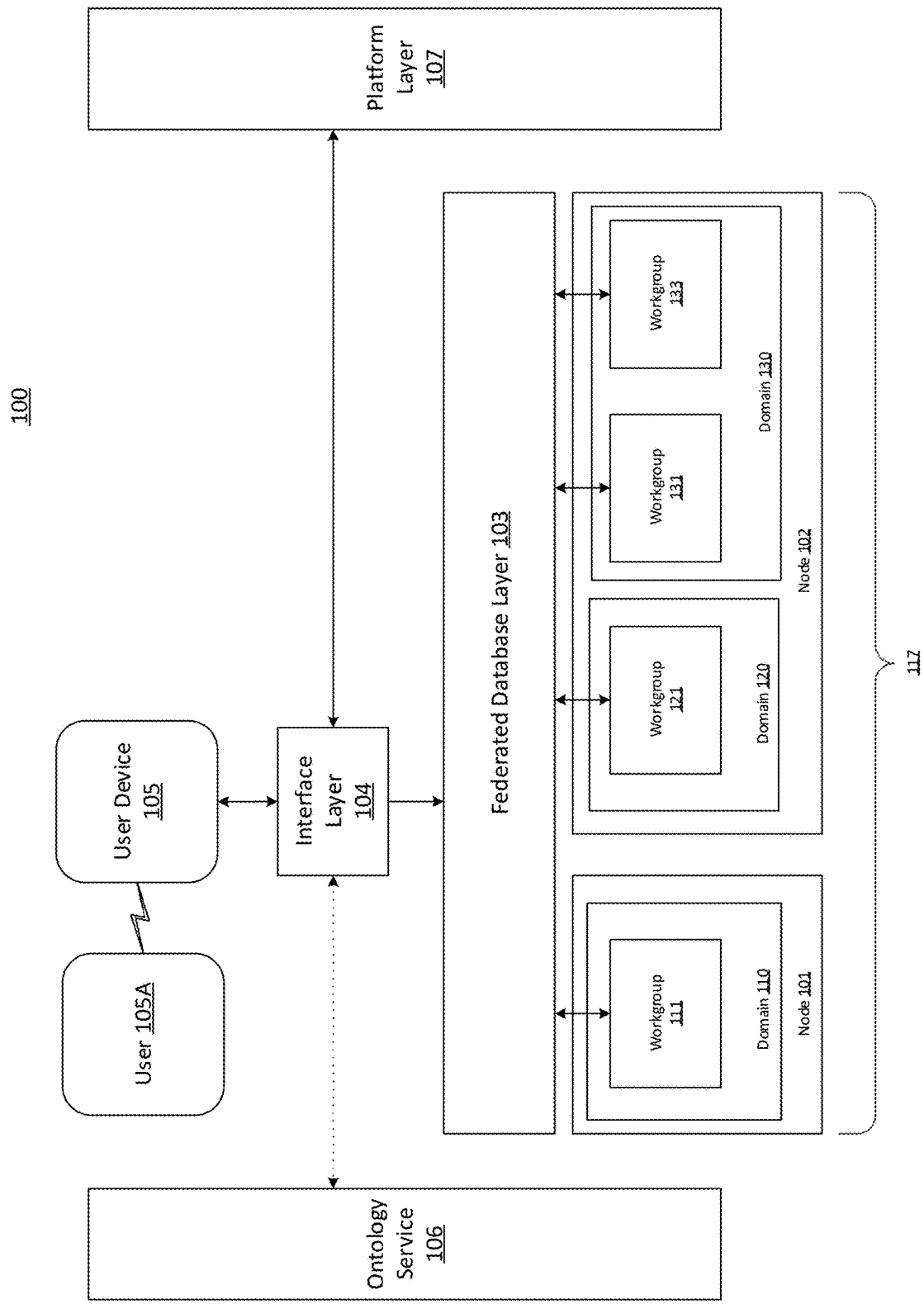
FIG. 1 depicts an exemplary schematic of a system for sharing medical data, according to an embodiment of the invention.

Reference will now be made in detail to the disclosed embodiments, examples of which are illustrated in the accompanying drawings. Wherever convenient, the same reference numbers will be used throughout the drawings to refer to the same or like parts.

The disclosed systems and methods may implement a software platform enabling users to share medical data across multiple domains without disclosing individual patient information. As a non-limiting example, users involved in genome interpretation and genetic diagnosis may interact with the disclosed systems and methods to share evidence about variant pathogenicity. In some embodiments, a diagnostic lab may comprise a domain on the platform. Information about genetic variants labeled pathogenic or benign may be privately and securely stored in a knowledgebase associated with the domain. In addition, users associated with the diagnostic lab can query the broader network upon encountering an unfamiliar genetic variant. The disclosed systems and methods may be configured to track aggregate statistics regarding genetic variants and observed phenotypes, providing statistical certainty of pathogenicity once a genetic variant has been observed a sufficient number of times in conjunction with a phenotype.

Clinical and research application of next-generation sequencing technology to disease diagnosis and treatment is in its early stages. An initial implementation of this technology has been in targeted panels, where subsets of cancer-relevant and/or highly actionable genes have been scrutinized for potentially actionable mutations. This approach has been widely adopted, offering high redundancy of sequence coverage for the small number of sites of known clinical utility at relatively low cost.

However, many more potentially clinically actionable mutations may exist both in known disease-related genes (such as cancer genes) and in other genes not yet identified as disease-related genes. Improvements in the efficiency of next-generation sequencing can make it possible to consider whole-genome sequencing (WGS) as well as other omic assays such as RNA sequencing (RNA-seq), but uncertainties remain in the status quo about how much additional useful information is available from these assays. Aside from cost, a challenge of WGS or whole-transcriptome data is the expertise and time required to interpret the full spectrum of genetic and somatic mutations. For example, genetic testing laboratories currently require up to 4 months to return genetic testing results, due to the lack of highly trained personnel to perform genome interpretation. There are also concerns about how to protect sensitive personal information of patients of various work groups, in regard to collaborations between the workgroups.

Embodiments of the invention may address bottlenecks in reporting the results of medical tests. The disclosed systems and methods may also enable collaborative analysis of medical data, such as collaborative annotation of genetic variants. The disclosed systems and methods may enable laboratories to collaborate with outside interpreters to speed reporting of test results. The disclosed systems and methods may also enable content providers to push medical data to the domains of users. Researchers, pharmaceutical companies, and other providers may access the disclosed system to locate patients with particular medical profiles, for example for studies or clinical trials.

As described below, medical data may be scrubbed of personally identifiable information when imported into the system and/or when retrieved in response to a request. Accordingly, disclosed systems and methods may not reveal personally identifiable information. Instead the disclosed systems and methods may reveal only general population-level medical data, such as aggregate population statistics. In this manner, the disclosed systems and methods may avoid disclosing the full medical data for a patient, preventing breaches of privacy. Also, by filtering corresponding meta data associated with particular queries, advantages of computational savings and bandwidth efficiencies can be achieved.

The disclosed embodiments may include a system for sharing data. This system may include at least one processor and at least one non-transitory memory. The at least one non-transitory memory may store instructions. When executed by the at least one processor, the instructions may cause the system to perform operations. The operations may include creating a first workgroup having a first knowledgebase. The first knowledgebase may be federated with a common knowledgebase and a second knowledgebase of a second workgroup. At least one of the first knowledgebase, common knowledgebase, and second knowledgebase may store data items comprising associations, signs, and evidence. The operations may also include receiving a request from a user in the first workgroup, the request comprising at least one of a first association and a first measurement. The operations may additionally include retrieving matching data items from at least one of the first knowledgebase, common knowledgebase, and second workgroup knowledgebase. The operations may also include outputting to the user at least some of the retrieved matching data items.

In some aspects, the first workgroup and the second workgroup may be associated with distinct entities. In various aspects, the second workgroup may be hosted on a second node distinct from a first node hosting the first workgroup. First data-sharing regulations may control provision of data by the first node, and differing second data-sharing regulations may control provision of data by the second node.

In some aspects, the operations may further comprise receiving data items from the user and storing the received data items in the first knowledgebase. In various aspects, the operations may further comprise receiving data items pushed from the common knowledgebase and storing the pushed data items in the first knowledgebase.

In some aspects, the operations may further comprise receiving another request from the second workgroup. This other request may comprise at least one of a second association and a second measurement. The operations may also comprise determining matching data items in the first knowledgebase, and providing the determined data items to the second workgroup. These determined data items may comprise personally identifiable information. The operations may additionally comprise removing the personally identifiable information before providing the determined data items to the second workgroup.

In some aspects, the first knowledgebase may comprise versions of the matching data items. The retrieved matching data items may satisfy a version criterion. The request may comprise the version criterion. The versions of the matching data items created after a date may satisfy the version criterion. In various aspects, the retrieved matching data items may satisfy a quality criterion.

In some aspects, the matching data items may be retrieved from the second knowledgebase. The operations may further comprise storing the matching data items in the first knowledgebase. In various aspects, the associations may comprise at least one of variant, exon, gene, copy number, and pathway associations. In some aspects, the associations may comprise at least one of Mendelian, prognostic, predictive, pharmacokinetic, prevalence, and classification associations. In some aspects, the data items may further comprise curation information.

The disclosed embodiments may include a non-transitory computer-readable medium storing instructions. When executed by at least one processor of a system, the instructions may cause a first node of the system to perform operations. The operations may include creating a first workgroup associated with a first entity. The first workgroup may have a first knowledgebase. The first knowledgebase may be federated with a common knowledgebase and a second knowledgebase of a second workgroup. The second workgroup may be associated with a second entity hosted on a second node of the system distinct from the first node. At least one of the first knowledgebase, common knowledgebase, and second knowledgebase may store versioned data items comprising associations, signs, and evidences. The operations may include storing, in the first knowledgebase, versioned data items. One of these versioned data items may be received from a user in the first workgroup. One of the versioned data items may be pushed from the common knowledgebase. One of the versioned data items may be shared by the second knowledgebase. The operations may further comprise receiving a request from the user, the request comprising a version criterion and at least one of an association and a measurement. The operations may also comprise retrieving matching data items that satisfy the version criterion from at least one of the first knowledgebase, common knowledgebase, and second knowledgebase. The operations may also comprise outputting to the user at least some of the retrieved matching data items.

In some aspects, first data-sharing regulations may control provision of data by the first node, and differing second data-sharing regulations may control provision of data by the second node.

In some aspects, the operations may further comprise receiving another request from the second workgroup. The other request may comprise at least one of a second association and a second measurement. The operations may include determining matching data items in the first knowledgebase and providing the determined data items to the second workgroup. In various aspects, the determined data items comprise personally identifiable information. The operations may further comprise removing the personally identifiable information before providing the determined data items to the second workgroup.

FIG. 1 depicts an exemplary schematic of system 100 for sharing genomics data. In some embodiments, system 100 may comprise nodes (e.g., node 101 and node 102), user device 105, interface layer 104, federated database layer 103, ontology services layer 106, and platform layer 107. The nodes may be configured to store medical data, such as genomics data, drug effectiveness data, and phenotype data. In some aspects, a user (e.g., user 105A) may interact with one or more components of system 100, such as user device 105, to retrieve, provide, or modify this medical data.

There has been a need for sharing comparable, similar and compatible data formats in the area of bulk genomic data. To address such a need, for example, the federated database layer 103 can be designed to check that data from external databases are compatible for federation with the system 100. This federated database layer 103 can thus integrate external databases for federation, exposing same data formats and APIs to the system. In other embodiments, wrappers associated with the federated database layer 103 can wrap around each of external knowledgebases and/or external knowledgebases' APIs to integrate in to the system.

This network may be any type of network (including infrastructure) that provides communications, exchanges information, and/or facilitates the exchange of information, such as the Internet, a Local Area Network, or other suitable connection(s) that enables system 100 to send and receive information between the components of system 100, between the components of system 100 and other systems, and between system 100 and other systems. System 100 may be implemented as a web service, and may be implemented in accordance with representational state transfer (RESTful) principles. In various aspects, system 100 may be configured to pass data between the components of system 100 as data objects, using formats such as JSON, XML, and YAML. System 100 may be configured to expose application program interfaces (APIs) for communicating between system components. In some aspects, these APIs may be generated using an API description language such as Swagger, WSDL2.0, and/or WADL.

There has been a need for a common system for access control, which can work across multiple, decentralized databases as well as cloud versus on-premises installations. Embodiments of the invention can implement access control using tenant-aware distributed application authentication, as disclosed in PCT/US2017/035982, the content of which is hereby incorporated by reference in its entirety. For example, in any of the examples herein, the task of authentication for access to federated system 117s and databases can be distributed among a plurality of application hosting platform instances (e.g., a platform cluster). For example, a request received at one instance can be redirected to another platform instance for validation. The platform can be engineered to be tenant-aware in that different tenants can specify (e.g., the system can receive and store in authentication configuration information) different primary authentication platform instances, different preferred identity providers, different locations at which application are to be hosted, or the like.

As described herein, such locations can be indications of different geographical locations for the different tenants. Similarly, a preferred primary authentication platform instance can be represented in configuration information as a location. Determining the primary instance can then take the form of determining an instance at the configured location.

So, although there can be a primary authority for authentication (e.g., a platform authentication service at a platform instance at a designated location), the databases themselves can be distributed at multiple platform instances in a platform cluster, and the platform instances of the cluster cooperate to achieve authentication via the primary authority.

As described herein, applications can perform some of the work related to authentication. For example, an application can fetch an authentication token from a client and submit an authentication request for the token (e.g., to check the validity of the authentication token) to a platform authentication service. If no authentication token is pre-sent, the application can so indicate to the platform authentication service, which can result in sign on or provisioning.

In any of the examples herein, an authentication token can take a variety of forms. In practice, a token is a value that can be generated, stored, communicated, and validated. As described herein, such tokens can be generated, managed, and stored as token records accessible by the primary authentication platform instance. Encryption and other techniques can be used for security purposes. Token generation can be delegated to another authority as desired.

Additional information can be included in the authentication token. For example, an indication of the primary (e.g., originating, issuing, etc.) authentication platform instance can be included with the authentication token. The process of determining which instance is the primary instance can thus be accomplished by inspecting the authentication token. During the token-generation process, requests are directed to the primary instance based on tenant-specific configuration information, and the primary instance adds an indication of itself into the authentication token. Subsequent requests can thus re-use such configuration information, whether it is confirmed in the configuration information itself or not.

The authentication token can be implemented as a session token. It can thus be generated during initial authentication of a user identifier or application identifier. It is thus associated with a log-on session of a client (e.g., user identifier or application identifier). When the session ends due to sign-off or timeout, the token can similarly be automatically invalidated.

The authentication token can comprise a bearer token. Such a bearer token can be validated with a secret key generated and maintained by the primary authentication platform instance. Different secret keys can be used for different tenants and different platform instances. User bearer and application bearer tokens can be implemented.

The authentication token can be generated by including various information into plaintext (e.g., a pseudorandom value, the tenant identifier with which the token is associated, access control, such as which applications are permitted, and the like). Such plaintext can then be encrypted with the primary authentication platform instance secret key to generate the authentication token. Subsequently, when the token is received, for validation, it can be decrypted and looked up in authentication token records (e.g., by the platform authentication service at the primary instance), which can indicate which user is associated with the authentication token. The user identifier need not be incorporated into the token itself. If the decrypted token indicates a tenant identifier that does not match the tenant identifier indicated in the authentication token records, it is rejected, regardless of the token value. Access control indicated in the token can also be respected (e.g., if an attempt is made to access an unauthorized application, the associated authentication request is not validated).

Because the authentication token is validated against a central record of tokens, the central record can be updated to indicate invalidity. For example, when a user logs off, the authentication token for the session can be invalidated. Similarly, a time out can be set so that a token automatically becomes invalid after a certain period of inactivity. The period for automatic invalidity can be configured on a tenant-by-tenant basis.

In practice, validation can be achieved by accessing a service that responds to requests for validation. For example, responsive to a request comprising an authentication token, a validation result can be received from the service. Validation can be achieved by comparing a provided authentication token against stored authentication token records. Records can include additional information, such as whether the token is still valid.

Validity can require further information, such as the associated tenant. Thus, when the authentication token is created for a given tenant identifier, it can be associated in token records as associated with the tenant identifier. Subsequently, authentication requests (e.g., requests from an application to determine the validity of an authentication token) can include the tenant identifier (e.g., which can be determined by the application because the application instance can be configured to accept requests for a single given tenant only). If the tenant identifier in the authentication request does not match, validity is not confirmed by the platform authentication service, regardless of the token value.

Because sessions can be conducted over a secure channel (e.g., SSL or the like), various attacks against authentication can be avoided due to the various features described herein, such as the tenant-identifier accompanying the authentication request.

The nodes (e.g., node 101 and node 102) may implement instances of a federated system 117, for example, consistent with disclosed embodiments. Each of the nodes may comprise multiple clusters, servers, workstations, desktops, or laptops, consistent with disclosed embodiments. In some embodiments, the nodes may be implemented using a cloud-based computing environment. For example, a node may be a virtual machine on a platform such as Amazon Web Services. However, in various embodiments, one or more nodes may not reside on a cloud computing platform. In some embodiments, the nodes may be configured to maintain a federated system 117 of databases of medical information. Multiple instances of the federated system 117 may be hosted by each of the nodes. In some embodiments, different nodes may be subject to different restrictions on sharing medical data. For example, a first node (e.g., node 101) may be geographically located in a first region with data-sharing regulations controlling provision of medical data by the first node, while a second node (e.g., node 102) may be geographically located in a second region with differing data-sharing regulations control provision of data by the second system.

In any of the examples herein, a location of where an application is to be hosted can be specified as a location in tenant-specific authentication configuration information. Such a location can comprise a physical location such as a geographical location (e.g., data center), jurisdiction (e.g., regulatory authority), region, or the like. For example, different countries can be specified for data containment, compliance, or resource allocation reasons. In some cases, a jurisdiction or region can contain more than one geographical location (e.g., different data centers can be at different geographical locations within a single region).

Tenant-specific configuration information can indicate that applications are to be hosted at a particular location. In practice, the application hosting platform can map locations to respective application hosting platform instances. For example, one or more instances can be implemented at a first location, and one or more instances can be implemented at a second location. The applications hosted at the instances are thus located at their respective locations. Similarly, when determining a primary instance, an instance located at a location indicated in configuration information can be used.

In any of the examples herein, specifying different primary authentication application hosting platform instances (e.g., for different tenants) can comprise specifying different locations.

So, tenant-specific configuration information can indicate that a first application is to be hosted within a first jurisdiction, and a second application is to be hosted within a second jurisdiction. The applications can then include logic that limits functionality to that permitted within the jurisdiction. For example, it may be desired for an application to persist data only within the geographical boundaries of the jurisdiction. The data is then physically located within the jurisdiction. The tenant-specific information can indicate that the application be hosted within the jurisdiction.

In any of the examples herein, a first application hosting platform instance can be within a first jurisdiction, and the second application hosting platform instance can be within a second, different jurisdiction. Tenant-specific configuration information can thus specify that different applications are to be hosted within different jurisdictions.

As described herein, users can continue to avail themselves of the applications without concern for where they are hosted because the authentication functionality of the platform can continue to authenticate seamlessly, regardless of at which platform instance an application is hosted.

As described below, the federated system 117 may enable restrictions on impermissible sharing of medical data.

Federated database layer 103 may comprise one or more programs enabling users of workgroups to retrieve medical data stored by other workgroups, consistent with disclosed embodiments. Federated database layer 103 may be configured to manage data sharing between workgroups in different domains (e.g., workgroup 111 and workgroup 121). In some aspects, federated database layer 103 may be configured to manage data sharing between workgroups in the same domain (e.g., workgroup 131 and workgroup 133). Federated database layer 103 may be implemented using programs residing on each node, or on each domain within each node.

In the area of bulk genomic data storage and retrieval, there has been a need for local encryption (on disk, "at rest") to protect bulk access of customer-private data so that users can only query for small data items such as a particular genetic variant. These encryption techniques can use protocols such as, for example, caching solutions such as Hadoop, ElasticSearch, Lucene, or So1R. Also, there has been a need for encryption "in motion" of all participating knowledgebases to protect customer-private data at large and to protect incoming queries from being caught. This can include SSL or HTTPS protocols. In this manner, man-in-the-middle attacks where someone can snoop the queries can be prevented because only the user can have access to the key. Techniques and methodologies found in PCT/US17/35982 can be used in embodiments of the invention. The platform handles workgroups on sequence hub is end-point to end-point or user to user. By using these user management access control, workbases cannot be determined (which queries are being sent to the federated system 117). Also, ePHI can protect the patient itself so data cannot be traced back.

Interface layer 104 may comprise one or more programs managing interactions between the user device 105, the ontology service 106, the federated database layer 103, and the platform layer 107. Interface layer 104 may be configured to translate between protocols used by components of system 100. Interface layer 104 may be configured to automatically convert requests received from another component of system 100 into one or more additional requests. For example, interface layer 104 may be configured to convert a request for information received from user device 105 into multiple requests. For example, interface layer 104 may be configured to convert the request into a request for expanded terminology from the ontology service 106, a request for authentication from platform layer 107, and a request for data from federated database layer 103. Interface layer 104 may be configured to synchronize and/or order such requests. For example, interface layer 104 may be configured to ensure that authentication requests precede ontology service requests, and that ontology service requests precede federated system 117 requests.

User device 105 may comprise a computing system configured to communicate with the other components of system 100, or another system. An exemplary component of user device 105 is described below with respect to FIG. 6.

User device 105 may be configured to exchange data or instructions with the nodes (e.g., node 101 and node 102) by interaction with interface layer 104, or another component of system 100. User device 105 may include, but is not limited to, one or more servers, workstations, desktops, or mobile computing devices (e.g., laptops, tablets, phablets, or smart phones). In some embodiments, user device 105 may be configured to enable interaction with user 105A. In some aspects, user device 105 may provide a graphical user interface for displaying information. The displayed information may be received by user device 105, or may be generated by user device 105. For example, the displayed information may include medical data, such as medical data retrieved from the nodes.

Consistent with disclosed embodiments, user 105A may interact with user device 105 to use system 100. In some embodiments, user 105A may interact with user device 105 to provide to the nodes (e.g., node 101 and node 102) at least one of medical data and a query. The medical data may comprise at least one of a biomarker, association, and evidence, as described below with regard to FIG. 4. The query may include at least one of a biomarker, association, and evidence, and may include query parameters restricting the results, as described below. The query may direct system 100 to provide the results to user device 105, or another system.

There has been a need for developing a common matching language that is inclusive and scalable across different levels of granularity. To address such a need, for example, ontology service 106 may comprise one or more computer programs configured to receive at least one term and provide related terms. For example, as described in detail below with regard to FIG. 5B, ontology service 106 may be configured to receive at least one search term from interface layer 104, or another component of system 100. Ontology service 106 may be configured to provide related terms within a semantic distance of the received at least one term, based on the received term, stored ontologies (described below), a semantic distance, and between-ontology differences between the stored ontologies. In some embodiments, at least one of the semantic distance and the between-ontology differences may be predetermined. For example, at least one of the semantic distance and the between-ontology differences may be provided by another component of system 100, such as interface layer 104, or may be predetermined, as discussed in greater detail in "Semantic Distance Systems and Methods for Determining Related Ontological Data," filed Aug. 22, 2017 and based on U.S. Ser. No. 62/378,873, the content of which is hereby incorporated by reference in its entirety.

In some embodiments, the semantic distance and the between-ontology differences may be pre-computed and be readily available at the time of a call. In some embodiments, half a dozen medical vocabularies or more and at least half a million concepts that have some sort of relatedness can be supported. The six or more ontologies can be ingested into the ontology system and then the distance between all 500,000 or 600,000 terms can be pre-computed against each other. By that, a backbone of terms can be created that can be understood by use of the ontology platform service. Each data point can be mapped pairwise to that backbone. The federated system 117 may or may not store multiples of these mappings. At the time of ingesting a new sign, the database may already know that five diseases are associated with the sign. And they could already compute up to a certain distance all related terms and store them directly. For example, some user might contribute an association (e.g., that a mutation is related to breast cancer in a causative way). Then at the time of the federated system 117 storing this association, the semantic ontology could be used to retrieve with a predetermined distance, for example maximum distance of, say, 1.5. In this example, this semantic ontology retrieval could return subtypes of breast cancer and even parent terms. It could store all these different terms and assume that all these are related to the genetic mutation originally queried. These pre-computed values can be stored up to a point at which a certain amount of information in the database may be updated. In these embodiments, it may not be necessary to compute mappings on the fly for incoming queries, limiting the need to process on the ontology database, and further saving computational efficiencies for new incoming queries.

In various embodiments, at least one of the semantic distance and the between-ontology differences may be determined based on at least one of the user, an indication received from user device 105, the search term, and the stored ontologies. For example, the user may interact with a graphical user interface of the user device 105 to select a semantic distance. As an additional example, a user may adjust the semantic distance by adjusting a control to specify a threshold semantic distance value. This control may be a knob, a spinner, a slider, or another similar control.

Ontology service 106 may be configured to determine search terms using stored ontologies. As used herein, an ontology may be a representation of a field of discourse, describing data in the field of discourse. An ontology may be defined by formal rules, and computing devices may be configured to use the ontology according to these formal rules. An ontology may comprise terms and may include definitions of the terms. The terms may be hierarchically organized. Various ontologies can be seen in FIG. 8. Such ontologies may be user-defined, defined by the entity operating system 100, or may be defined by another entity. Non-limiting examples of ontologies include SNOMED Clinical Terms, a collection of medical terms used in clinical documentation and reporting; RxNorm, a terminology of medications; Online Mendelian Inheritance in Man (OMIM), a catalog of genes and genetic disorders; Logical Observation Identifiers Names and Codes (LOINC), a standardized database for identifying medical laboratory observations; International Classification of Diseases, V9 (ICD9-CM), a system of diagnostic codes for classifying diseases; and the UMLS Metathesaurus, a compendium of biomedical concepts.

Ontology service 106 may be configured to determine semantic distances between potentially related terms. In some embodiments, ontology service 106 may be configured to calculate semantic distances using predetermined correspondences. For example, a predetermined correspondence may associate a first correspondence term in a first ontology with a second correspondence term in a second ontology. This association may have a predetermined semantic distance, which may be zero. Ontology service 106 may be configured to calculate the semantic distance between a requested term in the first ontology and a potentially related term in the second ontology as a sum of distances. For example, ontology service 106 may be configured to calculate this semantic distance as a function of the distance between the requested term and the first correspondence term, the distance between the second correspondence term and the potentially related term, and the predefined distance between the first and second corresponding terms. The semantic distance between the requested term and the first correspondence term may depend on a hierarchical separation between the requested term and the first correspondence term in the first ontology. Likewise, the semantic distance between the requested term and the first correspondence term may depend on a hierarchical separation between the potentially related term and the second correspondence term in the second ontology.

Platform layer 107 may comprise one or more computer programs that manage configuration information for system 100. For example, platform layer 107 may be configured to receive, provide, and/or store authentication information. This authentication information may enable authentication of users of system 100 (e.g., user 105A) or authentication of another process or system. In some aspects, this authentication information may include user names, passwords, authentication tokens, or other authentication information known to one of skill in the art. In various embodiments, platform layer 107 may be configured to receive, provide, and/or store access information. This access information may govern access to the data stored by workgroups (e.g., workgroup 111, workgroup 121, workgroup 131, and workgroup 133), as described below with respect to FIG. 2. Platform layer 107 may be configured to provide this information, or an indication based on this stored information, directly or indirectly to federated database layer 103 to enable federated database layer 103 to retrieve information from the workgroups. For example, platform layer 107 may store access control lists, or similar methods known to one of skill in the art, to control access to the subset of data stored by a workgroup and accessible to another workgroup. These access restrictions may differ for each pair of workgroups in system 100. In some embodiments, the authentication and/or access control information may be specified in a sharing agreement stored by system 100.

Domains (e.g. domain 110, domain 105, and domain 130) may be hosted on nodes, as described with regard to FIG. 1. Accordingly, domain 210 may be hosted on a different node than domain 220. Domains may not be geographically co-located, and may be subject to differing policies regarding sharing of medical data. Domains may be associated with entities, such as scientific, educational, governmental, medical, or business institutions. For example, a domain may be associated with a laboratory at a hospital or educational institution or with a private commercial laboratory. For example, a domain may be associated with an entity such as Quest Diagnostics, Mayo Clinic Health System, Genomics England, or the Center for Personalized Cancer Therapy. System 100 may be configured to establish sharing agreements between domains that govern the access of components of one domain to medical data stored by another domain. For example, a first domain may allow sharing of medical data with another domain to the limits established by relevant regulatory bodies in the geographic locale encompassing the node hosting the domain. As an additional example the entities associated with two domains may be competitors, and may therefore restrict sharing of medical data between these two domains.

Workgroups (e.g., workgroup 111, workgroup 121, workgroup 131, and workgroup 133) may be components of domains. Workgroups may be temporary or permanent, and may represent logical groupings within the entities associated with domains. For example, workgroups may comprise divisions within a medical sciences laboratory, such as a cytogenetics laboratory, molecular genetics laboratory, or biochemical genetics laboratory. As an additional example, workgroups may comprise project groups at a company, or facilities in different countries (e.g., in the United Kingdom or the United States), or at different locations within a country (e.g., a laboratory facility in Boston and a laboratory facility in New York). Domains may be configured to allow sharing between workgroups (e.g., workgroup 131 and workgroup 133), or may be configured to allow sharing between a workgroup in a domain and the workgroups within another domain (e.g., workgroup 121 and workgroup 133). As would be recognized by one of skill in the art, since domains may reside on separate nodes, a workgroup (e.g., workgroup 111) may be hosted on a system distinct from another system hosting another workgroup (e.g., workgroup 121).

Figure 2:
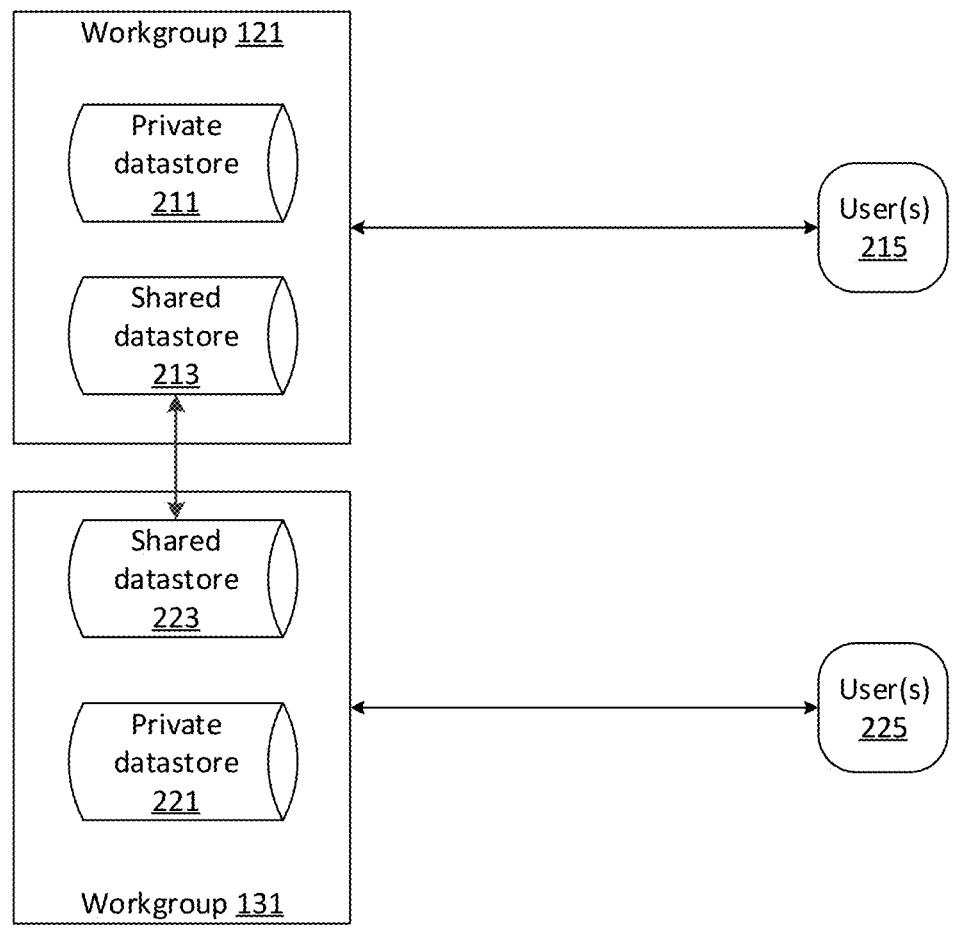
FIG. 2 depicts an exemplary logical description of knowledgebases and users, according to an embodiment of the invention.

FIG. 2 depicts an exemplary logical description of knowledgebases and users, consistent with disclosed embodiments. In some embodiments, knowledgebases may comprise collections of data items. The collections may be actual or logical. For example, when a node hosts a domain containing a workgroup, the node may also be configured to actually store the knowledgebases associated with the workgroup. Alternatively, or additionally, such a node may be configured to store access information enabling retrieval of the data items comprising the knowledgebase from some of the nodes (e.g., node 101 and node 102), or from another system.

Knowledgebases may comprise private datastores (e.g., private datastore 211 and private datastore 221) and shared datastores (e.g., shared datastore 213 and shared datastore 223). In some aspects, these private and shared datastores may be implemented as separate datastores. In various aspects, these private and shared datastores may be implemented as logical divisions in a single datastore. For example, a datastore management system, such as federated database layer 103, may manage access to a knowledgebase to enable authorized workgroups to access data items in a shared datastore (e.g., shared datastore 213 and shared datastore 223). As would be appreciated by one of skill in the art, different workgroups within a domain or domains may have differing degrees of access. A common knowledgebase may be a knowledgebase accessible to all workgroups in system 100. An entity, or a constituent of an entity, may interact with system 100 to establish a common datastore, for example as part of a subscription service.

Similarly, a private datastore (e.g., private datastore 211 and private datastore 221) may be inaccessible to users outside of a particular workgroup (e.g., outside of workgroup 121 for private datastore 211, or outside of workgroup 131 for private datastore 221). In some embodiments, private datastores may be configured to store medical data not intended for sharing. For example, private datastores may store data items including personally identifiable information, that is, information that could potentially identify a specific individual. In some embodiments, shared datastores may include such personally identifiable information, and a datastore management system, such as federate datastore layer 103, may be configured to remove the personally identifiable information before providing the medical data items to the second workgroup.

In some aspects, a datastore (e.g., shared datastore 213, shared datastore 223, private datastore 211, and private datastore 221) may be implemented as one or more relational datastores. In various aspects, such a datastore may be implemented as one or more "NoSQL" type datastores, such as document-oriented datastores. For example, the disclosed datastores may be implemented as elasticsearch datastores. In some embodiments, knowledgebases may be configured to implement versioning. This versioning may be implemented at a record or document level, according to methods known to one of skill in the art. In some embodiments, versioning criteria controlling versioning may be implemented by the datastore. For example, the datastore may be configured to automatically retain a predetermined number of previous versions. As an additional example, the datastore may be configured to intermittently generate a new version of a data item automatically. For example, the datastore may be configured to generate a new version of a date item periodically (e.g., every day).

System 100 may be configured to associate users (e.g. users 215 and users 225) with workgroups, consistent with disclosed embodiments. In some aspects, users may comprise data and instructions stored in memory, and may be associated with people, groups of people, and/or entities. Consistent with disclosed embodiments, system 100 may be configured to enable an entity associated with a domain to create users for the domain. In some aspects, system 100 may be configured to enable an entity associated with a domain to assign users for the domain to one or more workgroups within the domain. For example, system 100 may be configured to enable an entity to assign users 315 to workgroup 121.

Figure 3:
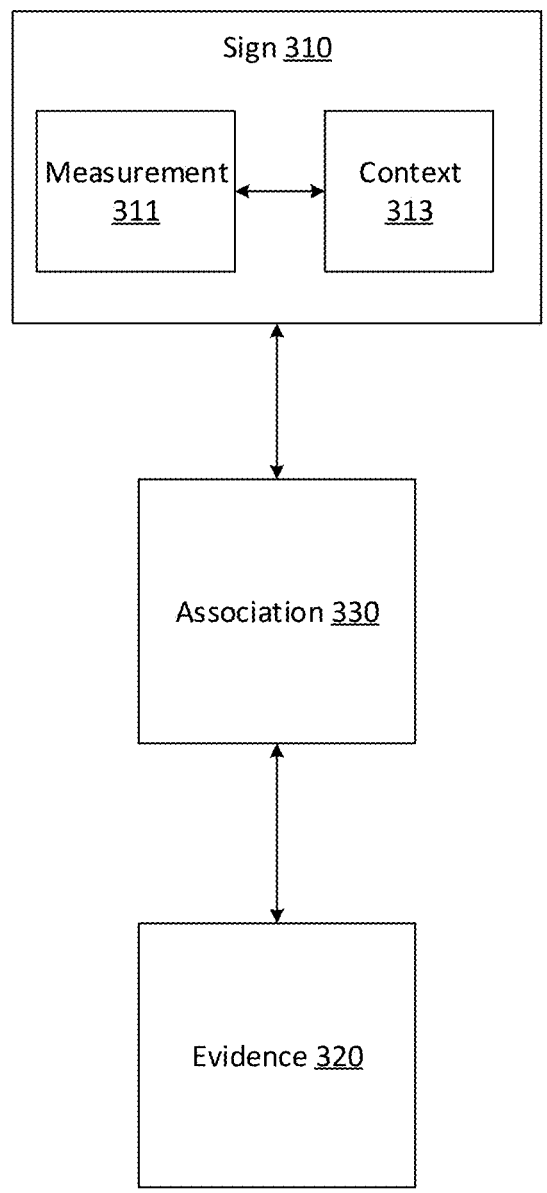
FIG. 3 depicts an exemplary component of a knowledgebase, according to an embodiment of the invention.

FIG. 3 depicts an exemplary data model of a data item in a knowledgebase, consistent with disclosed embodiments. In some embodiments, system 100 may be configured to store medical data comprising such data items in a datastore (e.g., shared datastore 213, shared datastore 223, private datastore 211, and private datastore 221). Knowledgebases may comprise collections of such data items. In some embodiments, these data items may include signs 310, evidences 320, and associations 330. In some embodiments, associations 330 may comprise data structures linking signs 310 to evidences 430. Thus system 100 may enable users to identify the meaning and potential impact of measurements 311 in a variety of contexts 313 using associations 330, upon a review of evidences 320.

Signs 310 may comprise objective medical indications and descriptions of the context of these objective medical descriptions. Signs 310 may comprise data or instructions stored in memory. For example, in some aspects, signs 310 may comprise measurements 311 and context 413. Measurements 311 may include genomic data for one or more patients, such as biomarkers. For example, measurements 311 may include biomarkers at the nucleotide, exon, gene, copy number, chromosome, or pathway level. As an additional example, measurements 311 may include DNA variant or single nucleotide polymorphism data, RNA expression level data (e.g., upregulation or downregulation information), protein formation data, copy number data, chromosomal abnormality data (e.g. translocation information), epigenic changes such as DNA methylation and/or histone acetylation, and other genomic information known to one of skill in the art.

Contexts 313 may include data describing contexts in which measurements 311 are relevant. In some aspects, a context may be a disease indication. The inclusion of the measurement and the context in the sign may indicate a relationship between the measurement and the disease indication. For example, a sign may include measurements concerning the gene BRAF-003 and the context lung cancer, as BRAF-003 is a proto-oncogene and may be associated with lung cancers. In various aspects, a context may be a drug. The inclusion of the measurement and the context in the sign may indicate a relationship between the measurement and the drug. For example, a sign may include measurements concerning the gene BRAF-003 (e.g., presence of the BRAF V600E mutation) and a context for the drug Citalopram. This sign may indicate that BRAF V600E mutation-positive patients may experience improved responses with this drug. In some aspects, this context may be a phenotype. For example, a sign may include measurements concerning the gene BRAF-003 and a context indicating a particular phenotype associated with these measurements. In some embodiments, multiple contexts may be associated with a measurement. For example, a measurement may be associated with one or more disease indications, drugs, and phenotypes. The sign data structure provides for an efficient way of directly linking measured biomarker data with disease indications, drugs, and phenotypes. This data structure can cut down on excess databases and corresponding information, thus saving storage space and improve efficiency in making calls.

Evidences 320 may comprise data relevant to the existence of the relationship indicated by signs 310. For example, evidences 320 may include information from publications (e.g., scientific publications, company webpages, textbooks, or similar publications), companion tests or companion diagnostics, treatment guidelines (e.g., treatment guidelines promulgated by a scientific, professional, or regulatory body), drug labels, or other sources of evidence (e.g., assertions by authorities on a relevant field, clinical trial results, case studies).

Associations 330 may comprise data further describing the association indicated by sign 410. In some aspects, for example, associations 330 may indicate at least one of a predictive (e.g., an increased likelihood of developing a disease), prognostic (e.g., increased likelihood of milder course of disease), or pharmokinetic (effect on drug pharmokinetics) relationship.

In some aspects, for example, associations 330 may indicate at least one of a Mendelian relationship (e.g., a distribution of phenotypes in accordance with Mendelian inheritance), a prevalence (e.g., the frequency of a measured biomarker in a population), and classification (e.g., a type of the biomarker). In various aspects, associations 330 may indicate the presence of a clinical trial.

In some embodiments, associations 330 may exist at a particular level of curation. For example, some associations may be established at the level of a variant, while others may be established at the level of an exon, gene or pathway. As described below with regards to FIG. 5, users of system 100 may curate knowledgebases, adding, removing, and modifying associations over time as new evidences become available, and new contexts are discovered. This curation may occur at multiple levels of curation, for example associations established at the level of variants may inform associations at the higher levels of exons, genes, or pathways. These associations 330 may comprise separate data structures stored in a knowledgebase. For example, a variant may result in a change in a biochemical pathway, which may in turn affect an organ system, resulting in a particular phenotype. According to the envisioned systems and methods, an association may be established between any combination of the variant, the biochemical pathway, the organ system, and the phenotype. These associations may be stored in different locations in the federated system 117. In this manner, system 100 may comprise multi-level, curated, federated system 117s and databases of associations between medical measurements and contexts.

One or more of signs 310, evidences 320, and associations 330 may include additional parameters. In some embodiments, these additional parameters may comprise versioning information, such as a version number or creation date. In various embodiments, these additional parameters may comprise curation information, such as an identifier of a curating entity. For example, one of associations 330 may include the Clinical Laboratory Improvement Amendments (CLIA) number of a laboratory. As an additional example, one of evidences 320 may include information identifying the entity or entities designing, funding, and/or executing a clinical trial. As a further example, a sign may include at least one of the name, title, and institution of a physician or researcher reporting one of signs 310. As would be appreciated by one of skill in the art, numerous other identifiers for various curating entities are possible, and the above examples are not intended to be limiting. In some embodiments, these additional parameters may comprise quality information. In some embodiments, quality information may comprise a ranking. In some aspects, quality information may be automatically assigned by system 100. For example, with regard to evidences 320, case reports may be assigned a lower ranking than multicenter clinical trials. As an additional example, measurements 311 may be ranked according to quality information indicia such as read depth, sequencing technology, number of probes, or other indicators of data quality. A user that pushes signs onto individual or external datastores can have such quality information indicia stored in a structure or semi-structured that can later be used to verify the trustworthiness of the data, as described below. In various aspects, quality information may be assigned by other users of system 100. For example, users may provide indications to system 100 of a quality ranking of a data item.

Figure 8:
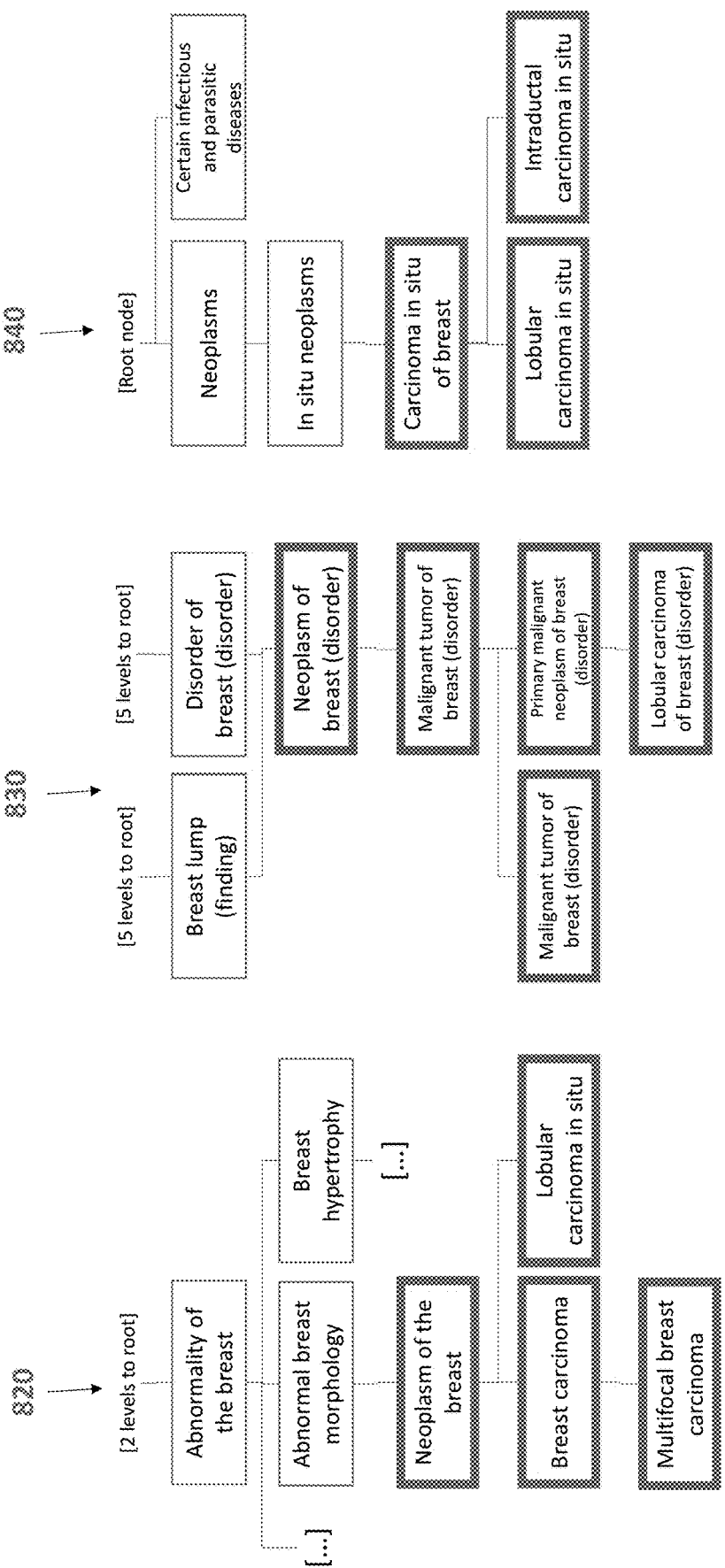
FIG. 8 depicts an example ontological system, according to an embodiment of the invention.

While knowledgebases can be user-generated having signs/associations/evidences as described above, a workgroup/knowledgebase may exclusively employ a specialized ontology of medical terms, such as ontology 820 as shown in FIG. 8, which can be "Ontology: HPO" and/or a second workgroup/knowledgebase such as ontology 830 as shown in FIG. 8, which can be "Ontology: SNOMED". The system is meant to translate between the ontologies overlapping content with other knowledgebases or datastores. Embodiments of the invention can overcome a technical need of users with large data sets using different terminologies and vocabularies, and to streamline computational resources for efficient lookup calls. FIG. 8 shows an example of how the process can be implemented. For example, as shown in FIG. 8, when a user searches for the query "Breast cancer", a first ontology HPO can be searched. Based on the semantic distance of the term "breast cancer" on the first ontology HPO, the term "neoplasm of the breast" satisfies the predetermined semantic distance. In this case, the predetermined semantic distance of a maximum distance is included in the query as the second input parameter. Because the term "neoplasm of the breast" was returned, the terms that fell underneath this term also satisfied the predetermined semantic distance. At the same time, the query "breast cancer" searched across the second ontology SNOMED can return different terms. For example, the highest match that satisfies the semantic distance criterion hierarchically is "Neoplasm of breast (disorder)". After that, all the terms underneath are also included as satisfying the semantic distance criterion. Finally, a third ontology 840 of FIG. 8, which can be ontology ICD-10, can be queried using the term "Breast cancer," the term "Carcinoma in situ of breast" can satisfy the semantic distance criterion. Each of the children nodes of this term also satisfy the semantic distance criterion. Thus, through this implementation across various ontologies, a much greater return of results is possible with a singularly precomputed mapping of all possible terms within the ontologies.

Some of these efficiency gains can be shown through an example searching through the HPO, UMLS, and SNOMED databases. In an example, HPO terms were mapped to SNOMED terms using prior techniques for a total of 2,805 mappings. HPO and SNOMED in some embodiments have a small overlap because SNOMED can include disease-only terms while HPO can include any human phenotype. This can represent 16.70% mappings. Thus, a disadvantage to the prior art searching in this example is that over 80% of terms are uncorrelated to another database. Making use of the cross-ontology distances, such as in this example of using an intermediary database UMLS, the number of mappings can increase to 7245, representing 28.20%. This can thus represent a substantial increase in the number of mappings and related terms, especially when six different ontologies are used.

The mappings can take place from external sources, which have different cadences of updates. HPO could be updated daily since the database has updated information on a daily basis. The database UMLS could be synchronized twice a year since UMLS has information added twice a year. A mapping could be run whenever there is an update to any of the databases. So it can be updated every new time we ingest. Thus, it does not have to be precomputed upon every time a query is executed, saving computational resources. This can especially be the case when there are 600,000 terms that are in the databases.

A problem with associations can arise with new information over time. In addition to keeping track of modified or changed attributes, sifting through high volumes of data can take time and processing time. This problem can be addressed, for example, through versioning, which keeps track of changes in associations.

Figure 4:
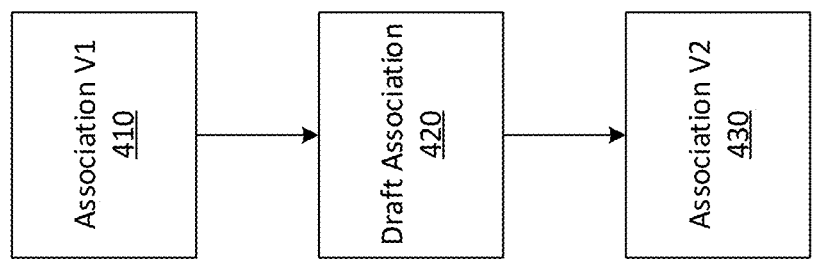
FIG. 4 depicts versioning of an association, according to an embodiment of the invention.

FIG. 4 depicts an exemplary flowchart illustrating a method of versioning associations. In some embodiments, system 100 may include the concept of roles. For example, system 100 may be configured to allow users associated with a knowledgebase and having a particular role in that knowledgebase to modify certain associations stored in the knowledgebase. For example, given a first version 410 of an association, system 100 may be configured to allow a user to create a draft version 420 of the association. This draft version may include additional evidences or contexts in the association, or otherwise modify the association, as would be understood by one of skill in the art. For example, a user may curate the association with notes and commentary. System 100 may be configured to allow the user, or another user, to progress the draft association to a second version 430 of the association. In some embodiments, when another user is required to progress the draft association, such a user may have a supervisory role over the user or users that created the draft association. In certain aspects, system 100 may be configured to associate a date and time stamp with second association 430. System 100 may be configured to use first version 410 as a default version until second version 430 is approved. Once second version 430 is approved, system 100 may be configured to make second version 430 the default version. For example, a default search of the federated system 117 may only return the default version of the association. However, a user may provide additional search parameters indicating that previous versions of associations should be returned.

As described above with regard to FIG. 4, system 100 may be configured to update versions of associations. This updating process may involve users acting as curators and reviewers for associations. In some embodiments, system 100 may be configured to receive requests to assign a curator for a data item. Such requests may be received from user device 105, or another system. In some aspects, a curator may be responsible for the annotation and validity of the data entry. A curator may be a user, or a group of users. In response to a request to assign a curator, system 100 may be configured to notify the curator. System 100 may also be configured to update the data item to identify the curator.

In some embodiments, system 100 may be configured to receive requests to assign a reviewer for a data item. Such requests may be received from user device 105, or another system. In some aspects, a reviewer may be responsible for authorizing the progress of a draft association to a final association, as described with regard to FIG. 4. A reviewer may be a user, or a group of users. In response to a request to assign a reviewer, system 100 may be configured to notify the reviewer. System 100 may also be configured to update the data item to identify the reviewer. System 100 may be configured to allow a reviewer to enable or disable an association.

FIGS. 5A-5D depict exemplary flowcharts for interactions with knowledgebases. In some embodiments, these interactions may occur as the result of users (e.g., user 105A) interacting with user devices (e.g. user device 105), or other components of system 100. Through these disclosed interactions, system 100 may enable users, workgroups, and domains to share medical data.

Figure 5A:
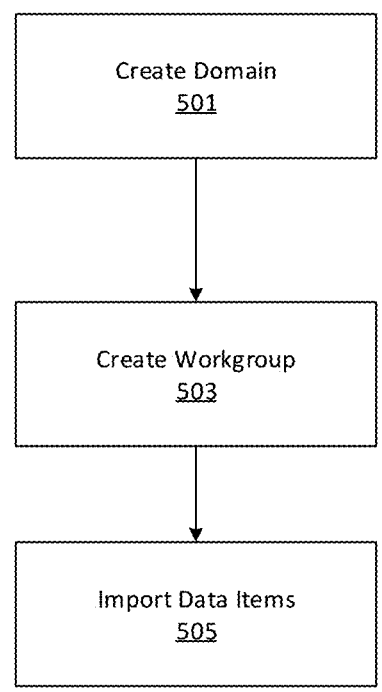
FIG. 5A depicts a flowchart for interactions with knowledgebases, according to an embodiment of the invention.

FIG. 5A depicts an exemplary flowchart of a method for creating a knowledgebase consistent with disclosed embodiments. In some embodiments, system 100 may be configured to create a new knowledgebase in response to indications received from a user (e.g., user 105A). These indications may be received as the result of interactions between the user and a user device (e.g. user device 105), or other component of system 100. In some aspects, the user may be a constituent of an entity, such as a scientific, medical, commercial, or governmental entity.

System 100 may be configured to create a new domain in step 501, consistent with disclosed embodiments. In some aspects, the nodes (e.g., node 101 and node 102) may be configured to create a new domain in response to indications received from user device 105, or another system. When the user is a constituent of an entity, the new domain may be associated with the entity. Nodes may be configured to use account information for the user and/or the entity to determine whether the user may create a new domain, or create a new domain on behalf of the entity. Similarly, nodes may be configured to use account information for the user and/or the entity to determine whether sharing agreements between the domain and other domains of system 100 exist, or may be created by the user. In some aspects, creating the domain may include creating user identities for the domain (e.g., users 315 and users 325).

System 100 may be configured to create a new workgroup in step 503. As described above with regard to FIG. 3, a workgroup may be temporary or permanent, and may represent logical groupings within the entity associated with the newly created domain. In some aspects, creating the workgroup may include creating user identities for the workgroup (e.g., users 315 and users 325), assigning users to the workgroup, and/or defining roles and privileges for users, or categories in the workgroup. In some aspects, the nodes (e.g., node 101 and node 102) may be configured to create templates for new users based on indications received from user device 105, or another system. These templates may include pre-determined sets of roles and privileges. In some embodiments, a new knowledgebase may be associated with the new workgroup. In some aspects, nodes may be configured to allocate computer resources for storing medical data in the new knowledgebase. In various aspects, nodes may be configured to create the new knowledgebase as a mapping to existing stored medical data.

System 100 may be configured to import data items in step 505 to the new knowledgebase, consistent with disclosed embodiments. In some embodiments, system 100 may be configured to import data items from a common knowledgebase to the new knowledgebase. In some aspects, this common knowledgebase may be accessible to all domains of the nodes (e.g., node 101 and node 102). This common knowledgebase may be repeatedly updated with additional or revised medical data. In this manner, system 100 may provide a mechanism for disseminating new medical data and enabling new domains to quickly acquire sufficient medical data to provide informed treatment options to patients. For example, rare genetic mutations may only be seen at a few genetic testing facilities, but medical data about such mutations may be added to the common knowledgebase and thus made available to the domains of system 100.

System 100 may be configured to automatically push data items from the at least one common database. In some aspects, following creation of a new knowledgebase, the nodes (e.g., node 101 and node 102) may be configured to provision this newly created knowledgebase with at least a portion of the contents of the common knowledgebase. For example, a genetic lab may prepare a report for a clinician with reporting one or more genetic mutations. By comparing the patient with the federated system 117, one or more results can return. To make use of these returned results, these hits can be pushed or imported into the user's local database. Before such a push, the user can sign off on the imported result's curator's analysis as trusted. For example, if a result for a particular genetic variant returns a result that the variant is pathogenic for another individual, the user can determine whether the diseases are identical or similar enough or that the mutations are similar enough. So the first step can be to search for similar measurements, to go over similar results, and to decide when to trust and to import the similar results into the user's own knowledgebase, which can be then be shared with clinicians. In this way, the user can make the ultimate decision on which data to trust based on, for example, a threshold. Such provisioning may occur upon creation of the new knowledgebase. As an additional example, this provisioning may occur later, following receipt of some subsequent indication from user device 105. In some aspects, nodes may be configured to push updates of the common knowledgebase to other knowledgebases. For example, such updates may be pushed periodically.

In some embodiments, when a user makes use of a data point that they found that was contributed by someone else, and push it to the local datastore, this contributes to the pagerank of the user. So when a lab very often contributes information that is used and imported by others, the trustworthiness of the contributing lab increases. Nodes on the federated network can be ranked, which contributes information and then results can be sorted, which can subsequently be returned. On the other hand, if a variant is contradicted by other labs, the trustworthiness is decreased. Further, quality information described previously that are available in a structured or unstructured format can be used to further increase the trustworthiness of the contributor. For example, the system can add to or subtract from the trustworthiness score of the contributor based on the read depth, sequencing technology, number of probes, or other indicators of data quality, of the contributor's data, if available.

In some aspects, these updates may require the entities associated with the other knowledgebases to compensate the entity associated with the common knowledgebase. For example, these entities may pay a fee, such as a subscription fee, to the entity associated with the common knowledgebase.

System 100 may be configured to automatically push data items (e.g., storing any new information) according to parameters received from user device 105 or another system. For example, the nodes (e.g., node 101 and node 102) may be configured to receive an indication of desired associations 330, signs 310, and/or evidences 320; or categories of desired associations 330, signs 310, and/or evidences 320. In some aspects, the nodes (e.g., node 101 and node 102) may be configured to receive an indication that only signs 310 including measurements 311 at one or more particular association levels should be imported. For example, the particular association level may include the variant, exon, gene, or copy number curation levels, but not the pathway association level. Similarly, the nodes (e.g., node 101 and node 102) may be configured to receive an indication that only signs 310 including specific context 413 should be imported. For example, user device 105 may indicate to the nodes (e.g., node 101 and node 102) that signs 310 including drug or disease contexts should be imported, but not signs 310 including only phenotype contexts.

Figure 5B:
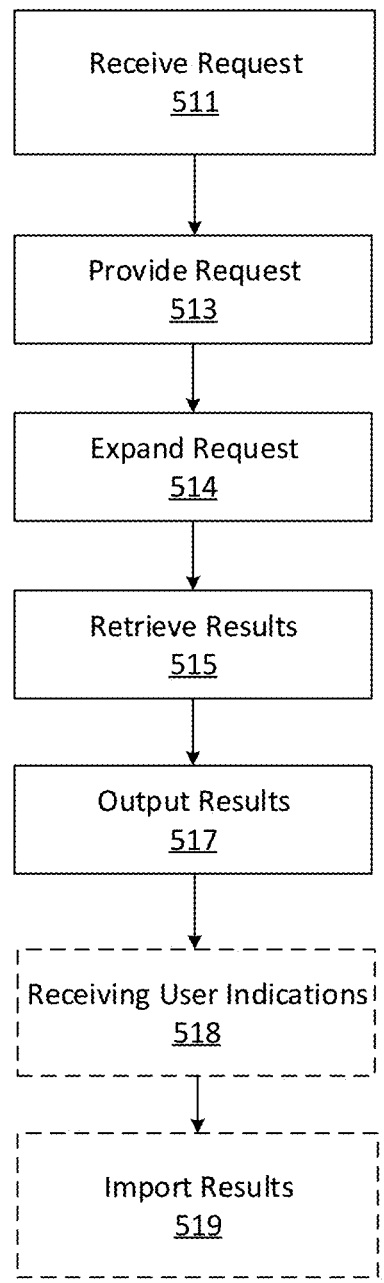
FIG. 5B depicts a flowchart for interactions with knowledgebases, according to an embodiment of the invention.

FIG. 5B depicts an exemplary flowchart of a method for requesting data items consistent with disclosed embodiments. This method may enable users of system 100 to efficiently and rapidly share medical information across geographically distinct regions, between institutions, and within institutions. Through the expanded search capability offered by ontology services 107, users may search nodes (e.g., node 101) for relevant data items through federated database layer 103, without knowing exactly what terminology is used by each node. An institution may upload data items to public datastore (e.g., shared datastore 223), and these data items may then become accessible to every user having a sharing agreement with the institution. However, the institution may keep data items private, and may disconnect from the federated system 117. Therefore the users of system 100 retain a degree of control over the stored data items. In some aspects, this exemplary method may include the steps of receiving the request, providing the request to interface layer 104, expanding the request, retrieving the results, and recording the results. The exemplary indication may further include receiving user indications, and importing the results into a knowledgebase.

System 100 may be configured to receive a request for data items in step 511, consistent with disclosed embodiments. For example, a node of the nodes (e.g., node 101 and node 102) may be configured to receive such a request. In some embodiments, the request may be received from user device 105, or another system. The request may indicate at least one of associations 330, signs 310, and evidence 320, and/or categories of associations 330, signs 310, and evidence 320. For example, the request may indicate all associations 330 related to a specified measurement 311. As a further example, the request may indicate all predictive associations 330 associated with a particular genetic variant. For example, the request may comprise a variant identifier, which may be a unique alphanumeric identifier associated with a variant. As an additional example, the request may indicate all measurements 311 related to a specified association 330 and context 313. As a further example, the request may indicate all measurements 311 associated with pharmacokinetic effects for a particular drug, or associated with a prognoses for a particular disease. As an additional example, the request may indicate all measurements 311 and all associations 330 related to a specified context 313. As a further example, the request may indicate all measurements 311 and associations 330 related to a particular phenotype.

In some embodiments, the request may include additional parameters. As described above with regard to FIG. 3, datastores (e.g., private datastores 311, shared datastores 313, private datastores 321, and shared datastores 313) may be configured to implement versioning. Consequently, in some aspects, the additional parameters may include a version criterion. This version criterion may be expressed as at least one of a status, version number, date, date range, or other identifier. For example, the version criterion may indicate a present version, previous version, original version, or other status indicating a relative location of a data item version within a collection of such versions. As an additional example, the version criterion may indicate version 1, version 10, or some other specific version number. As a further example, the version criterion may indicate the version existing on Jul. 12, 2016, or the most recent version before Jul. 12, 2016. The version criterion may specify or encompass a single version or multiple versions. In various aspects, the request may include a quality criterion. For example, the request may limit results to data items including multicenter clinical trials as evidence. As an additional example, the request may limit results to data items submitted by CLIA-certified labs, or a particular CLIA-certified lab. As a further example, the request may limit results to data items submitted by the Laboratory for Molecular Medicine. As a further example, as described below with regard to FIG. 5D, the request may limit results to data items having a community ranking (determined by system 100 using rankings provided by users of system 100) that is better than a certain threshold value. When a lab frequently contributes information that is used and imported by others, the trustworthiness of the data from the contributing lab can increase. As an additional example, the request may include a semantic distance. For example, the semantic distance may be a maximum semantic distance between the provided request and terms in an expanded request, as described below.

System 100 may be configured to provide the request to interface layer 104 in step 513, consistent with disclosed embodiments. In some aspects, interface layer 104 may be configured to handle tasks associated with fulfilling the request. For example, interface layer 104 may be configured to construct multiple secondary requests, based on the received request, and provide these secondary requests to other components of system 100. Interface layer 104 may be configured to provide these requests to other components in a particular order, which may be predetermined or may depend on the request. In some embodiments, interface layer 104 may be configured to authenticate user device 105 and/or user 105A using the authentication information stored in platform services 107. Additionally, or alternatively, in various embodiments federated database layer may be configured to authenticate user device 105 and/or user 105A using the authentication information stored in platform services 107.

In some embodiments, interface layer 104 may be configured to optionally provide a secondary request to ontological service 106, in step 514. In some aspects, this secondary request may include indications of the requested signs, associations, contexts, or measurements. For example, the secondary request may include a variant identifier, a disease name, a drug, or some other measurement, context, association, or evidence. Based on the received indication, stored ontologies, and a semantic distance, ontological service 106 may be configured to generate additional indicators. For example, the ontological service 106 may receive a disease name, such as "breast cancer," and a semantic distance value. Using the stored ontologies, ontological service 106 may be configured to determine additional indicators for other diseases within the received semantic distance of "breast cancer." For example, ontological service 106 may be configured to determine that "Invasive lobular carcinoma" and "Angiosarcoma" are within the semantic distance of "breast cancer," while "gunshot wound" is not. Such additional indicators may have a direct or indirect "is-a" relationship with the provided indicators. For example, the additional indicators may be ancestors or descendants of the provided indicator in an ontology. Ontological service 106 may be configured to use equivalences defined between ontologies to determine semantic distances across ontologies. Ontological service 106 may be configured to provide the additional indicators to interface layer 104. In this manner, system 100 may be configured to generate an expanded set of search terms for the federated system 117.

System 100 may be configured to retrieve results in step 515, consistent with disclosed embodiments. In some embodiments, interface layer 104 may be configured to provide a request for results to federated database layer 103. In some aspects, the request may include the search term(s) from the request received in step 511. In various aspects, the request may optionally include at least one of the expanded set of search terms generated by ontological services 106 in step 514.

In some embodiments, at least one of interface layer 104 and federated database layer 103 may be configured to limit routing of requests. Such limits may depend on sharing agreements between the domain or workgroup associated with the request and other domains in system 100, or regulations concerning medical data sharing governing a node (e.g., node 101 and node 102). In some aspects, at least one of interface layer 104 and federated database layer 103 may interact with platform layer 107 to determine knowledgebases accessible to the request. For example, interface layer 104 may be configured to provide the request, or an indication of the request to platform layer 107. As an additional example, federated database layer 103 may be configured to provide the request, or an indication of the request to platform layer 107. In response, interface layer 104 and/or federated database layer 103 may receive from platform layer 107 an indication of accessible knowledgebases, according to methods known to one of skill in the art. In some embodiments, these accessible knowledgebases may comprise only the publicly available portions of certain knowledgebases. In some embodiments, these accessible knowledgebases may comprise select portions of data of certain knowledgebases, according to the privileges assigned to the entity requesting access to the data.

In this manner, system 100 may prevent users from requesting data from a domain or workgroup unless the user and the domain or workgroup are party to a sharing agreement, or when satisfying the request would violate the sharing agreement. As a non-limiting example, satisfying a request contrary to regulations governing medical data sharing may violate a sharing agreement. Alternatively, or additionally, the requests may be denied by the instances of federated database layer 103 receiving the requests. For example, the instance of the federated database layer 103 on the node storing the requested data items may be configured to deny requests in the absence of a sharing agreement, or when the request contravenes a sharing agreement.

Federated database layer 103 may be configured to retrieve results from nodes (e.g., node 101 and node 102), consistent with disclosed embodiments. In some embodiments, federated database layer 103 may be configured to indicate search term(s) to one or more domains of system 100. In some aspects, the indications may comprise one or more data item identifiers. In some aspects, these data item identifiers may be associated with at least one of the requested associations 330, signs 310, or evidences 330. The data item identifiers may be unique within system 100. In some embodiments, federated database layer 103 may be configured to determine domain identifiers. This determination may be based on the data item identifier. For example, federated database layer 103 may be configured to maintain and/or access a mapping between domain identifiers and data item identifiers. This mapping may be one-to-one, many-to-one, or many-to-many. This mapping may be accomplished using techniques known to one of skill in the art. The particular techniques used are not intended to be limiting. The domain identifiers may be unique within system 100. In some embodiments, federated database layer 103 may be configured to determine the nodes (e.g., node 101 and node 102) corresponding to the mapped domain identifiers. For example, federated database layer 103 may be configured to maintain and/or access a mapping between domain identifiers and nodes. Each of the nodes may map to multiple domain identifiers.

Federated database layer 103 may be configured to route the request to another node that hosts a domain including the requested data item, consistent with disclosed embodiments. For example, when instances of the federated database layer 103 operate on the nodes (e.g., node 101 and node 102), and the request and the requested data items are associated with the same node, the instance of federated database layer 103 operating on the node may be configured to route the request to the domain storing the data items. Otherwise, the instance of federated database layer 103 may be configured to provide the request to the appropriate node or nodes of system 100. As described above, the remote node or nodes of system 100 may expose a web service, and the instance of federated database layer 103 may be configured to access this web service to retrieve the requested data items. For example, the instance of federated database layer 103 on the local node may be configured to provide the request to the remote node. The request may be formatted in JSON, YAML, XML, or a similar format.

Interface layer 104 may be configured to receive the requested data items, consistent with disclosed embodiments. The requested data items may be received from federated database layer 103. Interface layer 104 may then provide the requested data items to user device 105, or another system. In various embodiments, the requested data items may be directly received by user device 105, or another system. In some aspects, receiving the data items may encompass retrieving them from a local datastore. For example, when user 105A and/or user device 105 is part of a workgroup hosted on the same node that is storing the requested data items, receiving the request results may comprise retrieving them from the local datastore. In various aspects, the request results may be received from a remote node. For example, the data items may be received from a knowledgebase of another domain. This domain may be hosted on the remote node. In some embodiments, the request results may satisfy one or more of the additional request parameters described above. For example, the request results may satisfy a version criterion. As an additional example, the request results may satisfy a quality criterion. In some embodiments, one or more of the request results may include at least a portion of the data structure displayed in FIG. 3. As an example, when the request matches measurement 311, the request results may comprise the at least one of sign 310, association 330, and evidence 320.

In some embodiments, interface layer 104 may be configured to provide the retrieved data items to user device 105, or another system. In various embodiments, interface layer 104 may be configured to recode the retrieved data items before providing them to user device 105, or another system. In some embodiments, interface layer 104 may be configured to replace search terms present in the retrieved data items with one or more new search terms. These one or more new search terms may comprise a search term present in the request received in step 511. For example, when the request comprises the disease name "breast cancer," the expanded request includes the disease names "invasive lobular carcinoma" and "angiosarcoma." The retrieved data items may then indicate associations with "invasive lobular carcinoma" and "angiosarcoma." Interface layer 104 may be configured to recode these data items to indicate associations with "breast cancer." In some embodiments, interface layer 104 may be configured to provide at least a portion of the results to ontological services 106 as part of this recoding. In response, ontological services 106 may be configured to provide the one or more new search terms for recoding. In some embodiments, these one or more new search terms could be provided to federated database layer 103 to retrieve additional results.

Additionally, interface layer 104 can catalog a mapping of similar but not identical terms that are equivalent. For example, a research institute in England can use an ontology and/or datastore that includes data having a first degree of granularity that goes into detail about particular phenotypes and uses British American English. On the other hand, a hospital system or insurance company may use billing codes or groups of therapies that are more general than the first degree of granularity used by the British research institution. The hospital system and/or insurance company in America can internally use more general phenotypes to abstract phenotypes for one or more diseases. On top of this, it can use naming conventions stored in American English. To reconcile differences between the two, while at the same time preserving completeness and inclusiveness of data, the interface layer can translate on the backend equivalencies between terms by matching up equivalent terms across different ontologies. According to embodiments, this British research institution can enter a phenotype for searching according to British spelling of names and receive results in American English, for example, which can abstract any ontological differences to terms stored. In this manner, the search results and connections can expansively include terms that otherwise would not identically show up.

The interface layer can accomplish this by using an algorithm for matching across ontologies. See "Representation and Construction of Ontologies for Web Intelligence" by Li et al. (Proceedings of the IEEE/WIC Int'l Conf. Web Intelligence, 2003), incorporated herein by reference. Signs 310, evidences 320, and/or associations 330 for one ontology or datastore may be associated with a specific language or terminology that is different, but equivalent to signs 310, evidences 320, and/or associations 330 for another ontology or datastore. Thus, one ontology a research organization having a British spelling for terms can be included in the federated system 117 for comparison with another ontology having an American spelling of terms. A user with a preference set to a particular language or with a predominant knowledgebase of a particular language can input search terms in the federated search according to one language. Another parameter can be a particular level of generality for a term, such as a billing code for a hospital or insurance company that is more generic than a phenotype or disease that could be used by a research or clinical organization. The term can be compared for equivalent although not identical terms in other ontologies. Matches that satisfy the particular query can be returned in the equivalent language of the user even if it differs from the corresponding term in the federated system 117.

System 100 may be configured to output the data items in step 517, consistent with disclosed embodiments. In some embodiments, outputting the data items may comprise at least one of displaying and/or printing, storing, or providing at least a portion of the data items by a node (e.g., node 101) in response to the query in step 511. In certain aspects, nodes may be configured to store at least a portion of the data items in a non-transitory memory (e.g., memory 301). In various aspects, nodes may be configured to provide the data items to one or more other components of system 100, or to another system. For example, nodes may be configured to provide at least some of the data items to user device 105. User device 105 may be configured to perform at least one of displaying and/or printing, storing, or providing at least a portion of the data items. As would be recognized by one of skill in the art, displaying and printing may encompass a range of visual presentation methodologies, and the disclosed subject matter is not intended to be limited to a particular method.

System 100 may be configured to receive user indications in step 518, consistent with disclosed embodiments. In some embodiments, these indications may concern disclaimers or regulatory statements regarding the data. In some aspects, user 105A may be obligated to execute a disclaimer or regulatory statement prior to reviewing the data. For example, user 105A may be obligated to indicate that the data will be used for approved purposes. Similarly, user 105A may be obligated to release the original data provider and/or system 100 of any liability arising from the use of the data. System 100 may be configured to provide the disclaimers or regulatory statements. For example, system 100 may be configured to provide a disclaimer or regulatory statement to user system 105, or another system, for display. System 100 may be configured to track execution of the disclaimers or regulatory statements.

System 100 may be configured to import the received data items in step 519, consistent with disclosed embodiments. In some embodiments, the nodes (e.g., node 101 and node 102) may be configured to import the received data items in response to an indication. Nodes may be configured to receive this indication from user device 105 or another system. In some aspects, importing the received data items may comprise storing at least a portion of the received data items in a knowledgebase. In various aspects, the node that received the request may be configured to store at least a portion of the received items. The request may be associated with a workgroup, and the node that received the request may be configured to store at least a portion of the received data items in a knowledgebase associated with the workgroup.

In some embodiments, the imported data items may be merged with existing data items. For example, the knowledgebase may store an existing association between a sign and evidence, the sign including measurements and context. The requested data may include the association and sign, but include additional evidence. The node may be configured to then link the new evidence to the existing association. Similarly, new signs may be linked to an existing association, and existing signs may be updated with new contexts or new measurements. In some embodiments, the node may be configured to overwrite or delete one or more of components or values of the signs 310, evidences 320, and associations 330 upon importing the new data item. In various embodiments, the imported data items may comprise new versions of existing data items. In some aspects, the node may be configured to add the received data items to collections of versions of the data items. For example, a received data item may become the current version of a data item in a collection stored in the knowledgebase.

Figure 5C:
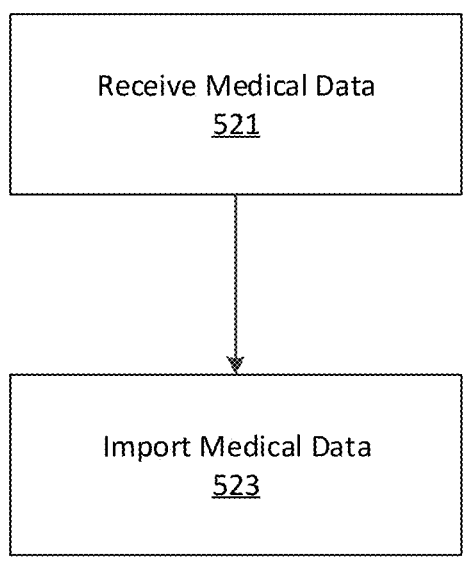
FIG. 5C depicts a flowchart for interactions with knowledgebases, according to an embodiment of the invention.

FIG. 5C depicts an exemplary method of adding medical data to a knowledgebase, consistent with disclosed embodiments. In step 521, system 100 may be configured to receive medical data from users. In some aspects, the medical data may comprise at least one component of a sign 410, evidence 320, or association 330. In various aspects, the provided medical data may comprise a measurement 311 or a context 413. For example, the provided medical data may comprise genomic information for a patient, such as variant information, exon information, epigenetic information, copy number information, chromosomal information, or pathway information. As an additional example, the provided medical data may comprise a description of a patient phenotype, a clinical diagnosis, or information concerning a drug. As a further example, the medical data may indicate a relationship between the measurement 311 and the context 413. For example, the medical data may comprise a prognosis, a prediction, a pharmacokinetic relationship, a prevalence, or a classification. The medical data may also include evidence supporting or contesting the asserted relationship. For example, the medical data may comprise descriptions of case studies showing that the asserted relationship is not valid, or a description of the results of a clinical trial. In some aspects, user 105A may provide the medical data directly, for example by entering the medical data using an input device such as a keyboard. In various aspects, user 105A may provide the medical data indirectly, for example by configuring user device 105, or another system, to automatically provide the medical data.

System 100 may be configured to import the data items in step 523, consistent with disclosed embodiments. In some embodiments, the node that received the medical data may be configured to convert the medical data into data items for storage in a knowledgebase. When the users are associated with a workgroup, the node may be configured to store the data items in a knowledgebase associated with the workgroup. In some embodiments, the medical data as provided may be expected to include personally identifiable information, while the stored data items may not be expected to include personally identifiable information. For example, a user of system 100 may expect that data items do not include personally identifiable information, while at the same time expecting that the medical data from which the data items was generated would include personally identifiable information. In some aspects, converting the medical data into data items may comprise removing personally identifiable information. In some embodiments, each use may be responsible for this anonymization. For example, each user of system 100 may be responsible for ensuring that personally identifiable information is not improperly input into system 100. For example, users in a certain node may be allowed to import personally identifiable information, so long as it remains in a private datasource of the workgroup, while other nodes may entirely forbid importation of personally identifiable information. In various embodiments, system 100 may be configured to prevent users from entering personally identifiable information into system 100. For example, data entry options may be limited to restrict the ability of users to inadvertently enter personally identifiable information. As an additional example, in some embodiments, data entry options may lack free text entry fields, or wizards or other configuration processes may be used to onboard data.

In various aspects, converting the medical data into data items may comprise validating the medical data. For example, system 100 may be configured to require the presence of certain data in a data item. In some aspects, the required data may depend on the value of the association. In various aspects, system 100 may be configured to require an association to import data items. For example, system 100 may be configured to require evidence to import data items, unless the association is a Mendelian association. As an additional example, system 100 may limit the evidence acceptable for an association. Furthermore, a clinical trial-type association may require clinical trial or publication evidence. In some embodiments, system 100 may be configured to automatically create associations 330 for the data item, based on the received medical data.

Figure 5D:
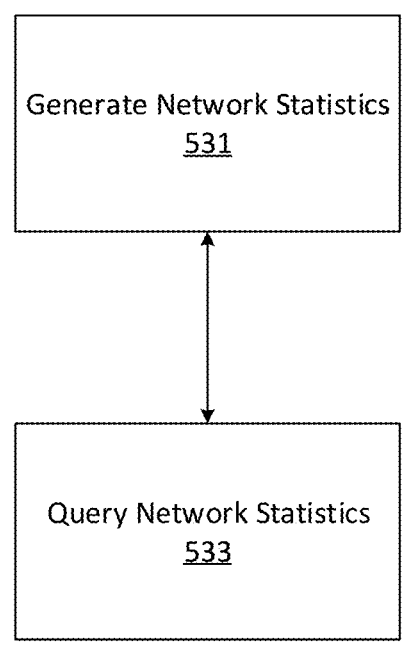
FIG. 5D depicts a flowchart for interactions with knowledgebases, according to an embodiment of the invention.

FIG. 5D depicts an exemplary method of generating network statistics for system 100. In step 531, system 100 may be configured to generate network statistics. In some embodiments, such statistics may concern interactions between users. For example, system 100 may be configured to track the number of times that users export data to, or import data from, other users of the federated system 117. System 100, or another system, may be configured to use these numbers to identify heavy consumers of data. Likewise, system 100, or another system, may be configured to use these numbers to identify users deemed reliable sources of information by other users. As would be appreciated by one of skill in the art, this pattern of data access and sharing between users could be analyzed for social network information according to methods known to one of skill in the art. In some aspects, system 100 may be configured to collect information concerning associations present within the system. For example, system 100 may be configured to track the number of distinct instances of a measurement present in the system. For example, given a genetic variant, system 100 may be configured to track the number of cases having that variant. System 100 may be configured to estimate a likelihood of pathogenicity based on factors including: a number of cases with that variant, the phenotype associated with reported cases having that variant, the number of users (or workgroups, domains, etc.) that have classified the variant as pathogenic, likely pathogenic, or of uncertain significance. Similar metrics could be established for other associations. For example, when a large number of cases, over the network as a whole, document the existence of a variant in the absence of a detrimental phenotype, system 100 may be configured to indicate that the variant is likely benign. In some embodiments, associations between measurements and contexts could generally be analyzed over the entire network. In some embodiments, data collection may be ongoing and automatic, according to methods known to one of skill in the art. In some aspects, the network statistics may be stored in the federated system 117. For example, they may be stored in a public workgroup accessible to all users of system 100. In some aspects, this public workgroup may be associated with the entity managing system.

System 100 may be configured to query network statistics, consistent with disclosed embodiments. In some aspects, a user of system 100 may query network statistics. This query may comprise running a special process or program over the federated system 117. The results of the special process or program may be the network statistics. Additionally, or alternatively, as discussed above, the network statistics may be stored on a public workgroup. The network statistics may then be accessible through the request process described in FIG. 5.

Figure 6:
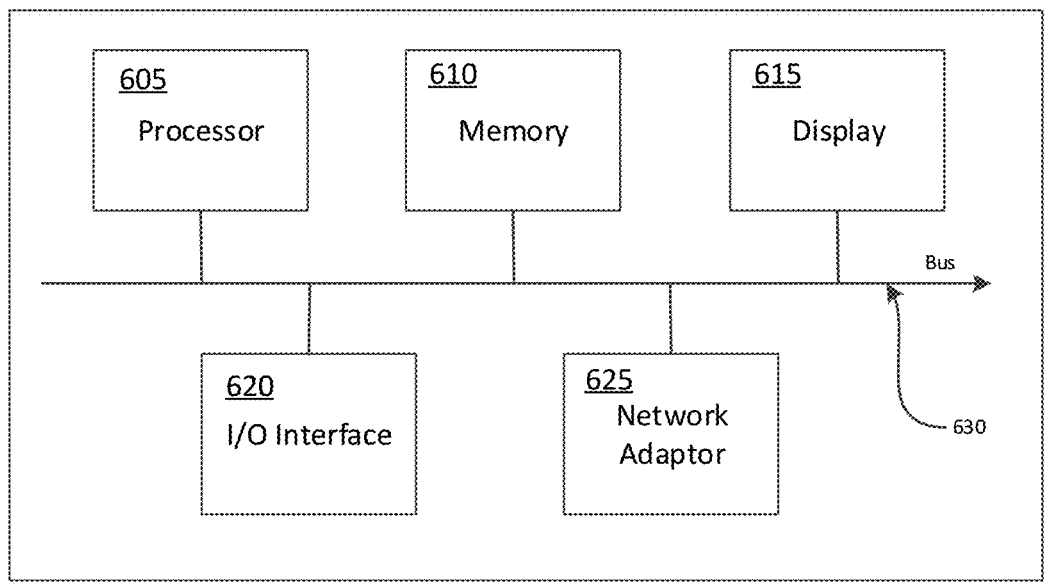
FIG. 6 depicts a computing system suitable for implementing the disclosed systems and methods.

FIG. 6 depicts exemplary computing system 600, suitable for implementing the disclosed systems and methods. Components of system 100, such as user device 105 and the nodes (e.g., node 101 and node 102), may be instances of exemplary computing device 600. According to some embodiments, computing device 600 may include a processor 605, memory 610, display 615, I/O interface(s) 620, and network adapter 625. These units may communicate with each other via bus 630, or wirelessly. In some embodiments, such instances of computing device 600 may include additional components, or may include fewer components. For example, certain implementations of computing device 600 may not include one or more of display 615, I/O interface(s) 620, and network adapter 625. The components shown in FIG. 6 may reside in a single device or multiple devices.

Processor 605 may be one or more microprocessors, central processing units, or graphics processing units performing various methods in accordance with disclosed embodiments. These processing units may include one or more cores. Memory 610 may include one or more computer hard disks, random access memory, removable storage, or remote computer storage. In various embodiments, memory 610 stores various software programs executed by processor 605. Display 615 may be any device which provides a visual output, for example, a computer monitor, an LCD screen, etc. I/O interfaces 620 may include a keyboard, a mouse, an audio input device, a touch screen, or a similar human interface device. Network adapter 625 may include hardware and/or a combination of hardware and software for enabling computing device 600 to exchange information with external networks. For example, network adapter 625 may include a wireless wide area network (WWAN) adapter, a Bluetooth module, a near field communication module, or a local area network (LAN) adapter.

Figure 7A:
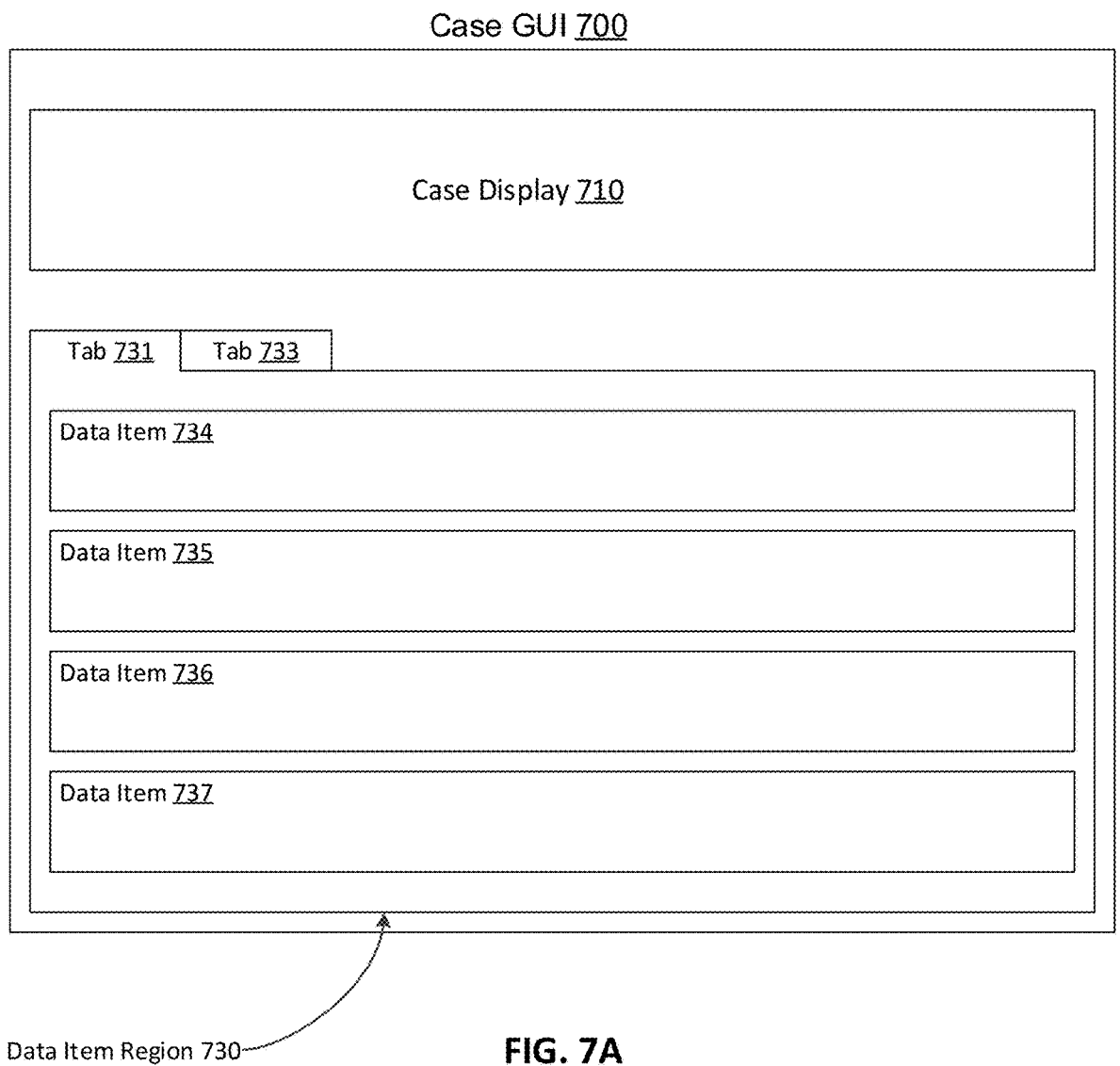
FIG. 7A depicts a graphical user interface suitable for implementing the disclosed systems and methods, according to an embodiment of the invention.
Figure 7B:
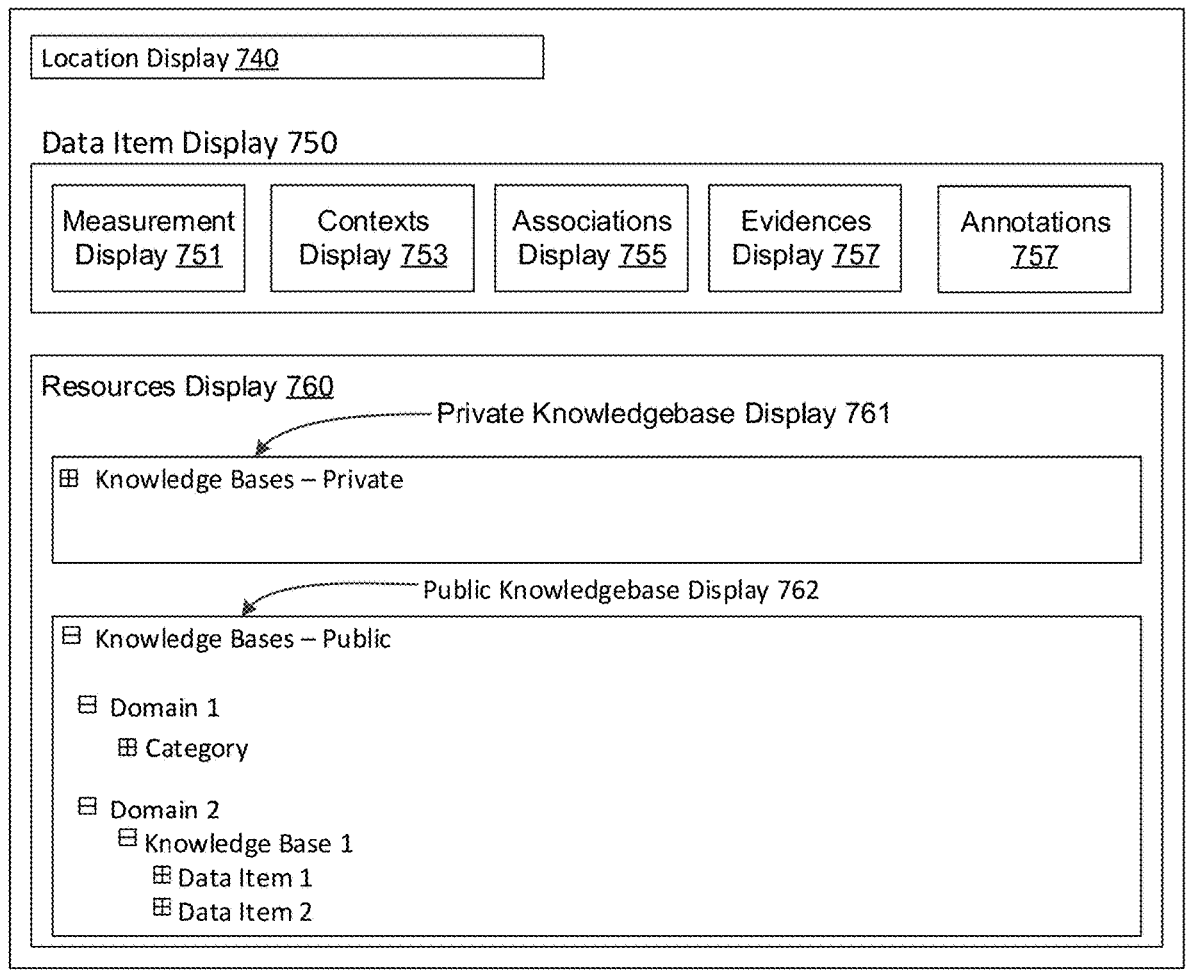
FIG. 7B depicts a graphical user interface suitable for implementing the disclosed systems and methods, according to an embodiment of the invention.

FIGS. 7A and 7B depict exemplary graphical user interfaces consistent with disclosed embodiments. In some embodiments, a user device (e.g., user device 105) may be configured to provide such a graphical user interface to a user (e.g., user 105A). Features of the disclosed systems and methods may be understood with regard to these graphical user interfaces.

FIG. 7A depicts an exemplary graphical user interface (Case GUI 700) for reviewing medical information of a case. In some embodiments, the case may be associated with, or concern, a patient. Case GUI 700 may comprise display regions. These display regions may include, for example, case information region 710 and data item region 730.

Case information region 710 may comprise general information about a case, including ID information, technical information, and personal information. ID information may include a unique identifier or filename for the case, which may comprise an alphanumeric string. Technical information may describe the process or processes used to generate the medical information. For example, when the medical information is genomic information, the technical information may describe at least one of the analysis pipeline, the reference genome build, a sample identifier of the sequenced sample, which may comprise an alphanumeric string, and a sample class (e.g., germline, somatic, cancer). Personal information may describe information about the patient. This personal information may enable identification of the patent, and distribution of this information may be subject to regulation, as would be appreciated by one of ordinary skill in the art. The personal information may include patient name, patient identifier, patient sex, contact information, and family information.

Data item region 730 may comprise multiple tabs (e.g., tab 731 and tab 733). A user may interact with data item region 730 to switch between tabs. Each tab may display a list of a particular type of data item (e.g. data item 734-data item 737). Tabs may be sorted, such that the list is an ordered list, and each tab may include interactive controls for sorting the displayed data items within the tab. Data items, as described above with regard to FIG. 3, may include signs 310, associations 330, and evidences 320. The displayed data items within the tab may include at least a portion of these signs 310, associations 330, and evidences 320. The displayed data items may be selectable. In some embodiments, selection of a displayed data item may cause system 100 to perform a search, as described above with regards to FIG. 5B. The results of this search may be displayed in a data item details view, as described below with regard to FIG. 7B.

FIG. 7B depicts an exemplary graphical user interface (data details GUI 701) for reviewing data items. In some embodiments, data details GUI 701 may comprise a location display 740, data item display 750, and resources display 760. In some embodiments, the reviewed data items may be retrieved by system 100. For example, the reviewed data items may be retrieved by system 100 following a user request, as described above with regards to FIG. 5B. In various embodiments, a user (e.g., user 105A) may interact with data details GUI 701 to browse available data sources.

The location display 740 may comprise information identifying the physical or logical location of the data item in system 100. As a non-limiting example, location display 740 may comprise a path to a computer resource, or a logical alias identifying a computer resource. In some aspects, the displayed data item may be accessible using this computer resource.

The data item display 750 may display information contained in the data item. For example, the data item display may include at least a portion of measurements 311 (e.g. measurement display 751), contexts 313 (e.g. contexts display 753), associations 330 (e.g. associations display 755), and evidences 320 (e.g. evidences display 757). The information displayed may be drawn from the contents of these data structures, which are described above with regard to FIG. 3. In some embodiments, the information displayed may comprise controls for measurement display 751, contexts display 753, associations display 755, and evidences display 757, that when selected cause system 100 to provide more information regarding the displayed measurement, context, association, and/or evidence. The data item display may also include annotations 759. These annotations may be provided by other users of system 100, or by the user viewing data item display 750. The displayed annotations may be user-editable.

The resources display 760 may include selectable controls corresponding to knowledgebases. In some embodiments, the displayed knowledgebases may include the containing information regarding the data item of data item display 750.

For example, the knowledgebases displayed may be those containing associations relevant to the data item of data item display 750. As an additional example, the knowledgebases displayed may be those containing associations for the same genomic variant, the same pathway, the same phenotype, the same disease, or the same drug. In some embodiments, resources display 760 may include a private knowledgebase display 761 and a public knowledgebase display 762. The private knowledgebase display 761 may include those knowledgebases associated with the user, or accessible to the user. For example, when the user is associated with "domain 1", then knowledgebases associated with "domain 1" (e.g. private datastore 211 and shared datastore 213) may be displayed in knowledgebase display 761. Additionally, when "domain 1" has a sharing agreement with "domain 2" then knowledgebases of "domain 2" included in this sharing agreement may be displayed (e.g. shared datastore 223). Public knowledgebase display 762 may be structured as an expandable list comprising levels and sublevels. In some embodiments, the levels may be descriptive of physical or logical locations. For example, when a level comprises a node (e.g., node 101), selecting the node may cause system 100 to display domains (e.g., domain 120) within the level as sublevels, as shown in FIG. 7B. Likewise, when the level comprises a domain (e.g. domain 130), selecting the domain may cause system 100 to display workgroups (e.g., workgroup 131) within the level as sublevels, as shown in FIG. 7B. Similarly, when a level comprises a workgroup (e.g. workgroup 131), selecting the workgroup may cause system 100 to display relevant data items stored in knowledgebases of the workgroup within the level as sublevels. In some embodiments, the levels may be descriptive. For example, the levels may describe categories of associations 330, such as predictive, prognostic, molecular classification, and clinical trial, as described above. Similarly, the levels may describe categories of evidences 320 and signs 310.

As shown in FIG. 7B, a user may interact with resources display 760 to traverse the expandable lists to locate one or more relevant data items. In some embodiments, selecting such a data item may cause system 100 to display details of the data item in data item display 750, or another display. In this manner, a user (e.g. user 105A) may interact with resources display 760 to retrieve relevant data items from knowledgebases accessible through federated database layer 103.

The foregoing disclosed embodiments have been presented for purposes of illustration only. This disclosure is not exhaustive and does not limit the claimed subject matter to the precise embodiments disclosed. Those skilled in the art will appreciate from the foregoing description that modifications and variations are possible in light of the above teachings or may be acquired from practicing the inventions. In some aspects, methods consistent with disclosed embodiments may exclude disclosed method steps, or may vary the disclosed sequence of method steps or the disclosed degree of separation between method steps. For example, method steps may be omitted, repeated, or combined, as necessary, to achieve the same or similar objectives. In various aspects, non-transitory computer-readable media may store instructions for performing methods consistent with disclosed embodiments that exclude disclosed method steps, or vary the disclosed sequence of method steps or disclosed degree of separation between method steps. For example, non-transitory computer-readable media may store instructions for performing methods consistent with disclosed embodiments that omit, repeat, or combine, as necessary, method steps to achieve the same or similar objectives. In certain aspects, systems need not necessarily include every disclosed part, and may include other undisclosed parts. For example, systems may omit, repeat, or combine, as necessary, parts to achieve the same or similar objectives. Accordingly, the claimed subject matter is not limited to the disclosed embodiments, but instead defined by the appended claims in light of their full scope of equivalents.

What is claimed is:

1. A computer system for sharing data, comprising:
   at least one processor; and
   at least one non-transitory memory, the at least one non-transitory memory storing instructions that, when executed by the at least one processor, cause the system to perform operations comprising:
   maintaining or accessing a federated system comprising a common knowledgebase, a first workgroup having a first knowledgebase, and a second knowledgebase of a second workgroup, wherein the federated system comprises a data structure that is configured to store categories for signs, associations, and evidences of variant data, and wherein the common knowledgebase, the first knowledgebase and the second knowledgebase are connected through a federated layer;
   storing data items in the federated system, the data items comprising the signs, associations, or evidence, the category for signs storing biomarker measurements and contexts of phenotypes, diseases or drugs, the category for associations storing an association between at least a biomarker measurement and a context, and the category for evidence storing information supporting the associations;
   generating statistics concerning associations stored within the federated system, wherein the statistics track or count a number of distinct instances of a respective measurement stored within the federated system, wherein the respective measurement corresponds to a genetic variant, and wherein the step of generating statistics utilizes associations, measurements and context analyzed over the entire federated system;
   estimating a likelihood of pathogenicity of the genetic variant based at least on the number of distinct instances of the respective measurement stored within the federated system, wherein estimating the likelihood of pathogenicity of the genetic variant comprises tracking aggregate statistics regarding a plurality of genetic variants and observed phenotypes and determining a statistical likelihood of pathogenicity of the genetic variant when the genetic variant has been observed a threshold number of times in conjunction with a phenotype; and
   outputting the likelihood of pathogenicity of the genetic variant.

2. The system of claim 1, wherein first data-sharing regulations control provision of data by a first node associated with the first knowledgebase, and differing second data-sharing regulations control provision of data by a second node associated with the second knowledgebase.

3. The system of claim 1, wherein the at least one non-transitory memory further stores instructions that, when executed by the at least one processor, cause the system to perform operations comprising receiving data items from a user and storing the received data items in the first knowledgebase.

4. The system of claim 1, wherein the at least one non-transitory memory further stores instructions that, when executed by the at least one processor, cause the system to perform operations comprising receiving data items pushed from the common knowledgebase and storing the pushed data items in the first knowledgebase.

5. The system of claim 1, wherein data items are retrieved from the second knowledgebase and stored in the first knowledgebase.

6. The system of claim 1, wherein the associations comprise at least one of variant, exon, gene, copy number, and pathway associations.

7. The system of claim 1, wherein the associations comprise at least one of Mendelian, prognostic, predictive, pharmacokinetic, prevalence, and classification associations.

8. The system of claim 1, wherein the data items further comprise curation information.

9. The system of claim 1, wherein the context is a disease.

10. The system of claim 1, wherein estimating the likelihood of pathogenicity of the genetic variant is based on factors that comprise at least a number of reported cases stored in or accessible by the federated system identified as having the genetic variant.

11. The system of claim 1, wherein estimating the likelihood of pathogenicity of the genetic variant is based on factors that comprise at least a respective phenotype associated with reported cases having the genetic variant.

12. The system of claim 1, wherein estimating the likelihood of pathogenicity of the genetic variant is based on factors that comprise at least a number of users, workgroups, or domains of the federated system that have classified the genetic variant as pathogenic, likely pathogenic, or of unclassified significance.

13. The system of claim 1, wherein the step of generating statistics concerning associations stored within the federated system utilizes associations, measurements and context analyzed over a public or shared portion of the federated system.

14. The system of claim 1, wherein the step of generating statistics concerning associations stored within the federated system automatically tracks and updated aggregate statistics regarding genetic variants and/or observed phenotypes as data is collected by the federated system.

15. The system of claim 1, wherein one or more of the steps of generating statistics, estimating the likelihood of pathogenicity of the genetic variant, or outputting the likelihood of pathogenicity of the genetic variant are performed in response to a user querying the federated system regarding the genetic variant.

16. The system of claim 1, wherein the at least one non-transitory memory further stores instructions that, when executed by the at least one processor, cause the system to perform further operations comprising:
determining that the genetic variant is benign when a threshold number or percentage of cases stored on or accessible by the federated network indicate the existence of the genetic variant in the absence of a detrimental phenotype; and
outputting an indication that the genetic variant is benign.

17. A non-transitory computer-readable medium storing instructions that, when executed by at least one processor of a system, cause one or more computing devices of the system to perform operations comprising:
maintaining or accessing a federated system comprising a common knowledgebase, a first workgroup having a first knowledgebase, and a second knowledgebase of a second workgroup, wherein the federated system comprises a data structure that is configured to store categories for signs, associations, and evidences of variant data, and wherein the common knowledgebase, the first knowledgebase and the second knowledgebase are connected through a federated layer;
storing data items in the federated system, the data items comprising the signs, associations, or evidence, the category for signs storing biomarker measurements and contexts of phenotypes, diseases or drugs, the category for associations storing an association between at least a biomarker measurement and a context, and the category for evidence storing information supporting the associations;
generating statistics concerning associations stored within the federated system, wherein the statistics track or count a number of distinct instances of a respective measurement stored within the federated system, wherein the respective measurement corresponds to a genetic variant, and wherein the step of generating statistics utilizes associations, measurements and context analyzed over the entire federated system;
estimating a likelihood of pathogenicity of the genetic variant based at least on the number of distinct instances of the respective measurement stored within the federated system, wherein estimating the likelihood of pathogenicity of the genetic variant comprises tracking aggregate statistics regarding a plurality of genetic variants and observed phenotypes and determining a statistical likelihood of pathogenicity of the genetic variant when the genetic variant has been observed a threshold number of times in conjunction with a phenotype; and
outputting the likelihood of pathogenicity of the genetic variant.

18. The non-transitory computer-readable medium of claim 17, wherein the operation of estimating the likelihood of pathogenicity of the genetic variant is based on factors that comprise at least one of:
a number of reported cases stored in or accessible by the federated system identified as having the genetic variant;
a respective phenotype associated with reported cases having the genetic variant; or
a number of users, workgroups, or domains of the federated system that have classified the genetic variant as pathogenic, likely pathogenic, or of unclassified significance.

19. The non-transitory computer-readable medium of claim 17, wherein one or more of the operations of generating statistics, estimating the likelihood of pathogenicity of the genetic variant, or outputting the likelihood of pathogenicity of the genetic variant are performed in response to a user querying the federated system regarding the genetic variant.

20. A computer-implemented method for sharing data, comprising:
maintaining or accessing a federated system comprising a plurality of processors and a plurality of storage devices, the federated system further comprising a common knowledgebase, a first workgroup having a first knowledgebase, and a second knowledgebase of a second workgroup, wherein the federated system comprises a data structure that is configured to store categories for signs, associations, and evidences of variant data, and wherein the common knowledgebase, the first knowledgebase and the second knowledgebase are connected through a federated layer;
storing data items in the storage devices of the federated system, the data items comprising the signs, associations, or evidence, the category for signs storing biomarker measurements and contexts of phenotypes, diseases or drugs, the category for associations storing an association between at least a biomarker measurement and a context, and the category for evidence storing information supporting the associations;

generating statistics concerning associations stored within the federated system, wherein the statistics track or count a number of distinct instances of a respective measurement stored within the federated system, wherein the respective measurement corresponds to a genetic variant, and wherein the step of generating statistics utilizes associations, measurements and context analyzed over the entire federated system;

estimating a likelihood of pathogenicity of the genetic variant based at least on the number of distinct instances of the respective measurement stored within the federated system, wherein estimating the likelihood of pathogenicity of the genetic variant comprises tracking aggregate statistics regarding a plurality of genetic variants and observed phenotypes and determining a statistical likelihood of pathogenicity of the genetic variant when the genetic variant has been observed a threshold number of times in conjunction with a phenotype; and outputting the likelihood of pathogenicity of the genetic variant.

21. A computer system for sharing data, comprising:
at least one processor; and
at least one non-transitory memory, the at least one non-transitory memory storing instructions that, when executed by the at least one processor, cause the system to perform operations comprising:
maintaining or accessing a federated system comprising a plurality of knowledgebases participating in the federated system, wherein the plurality of knowledgebases are connected via by a federated layer;
receiving a query from a user of the federated system, the query comprising at least an indication of a generic variant, wherein the query is configured to execute against a data structure stored on the federated system;
in response to the query, performing a federated search through the federated layer on the plurality of knowledgebases participating in the federated system;
in response to the federated search, receiving summary statistics generated at some or all of the knowledgebases participating in the federated system such that each responsive knowledgebase provides summary statistics responsive to the query, wherein the summary statistics track or count a number of distinct instances of a respective measurement stored within the federated system, wherein the respective measurement corresponds to the genetic variant, and wherein the summary statistics are generated utilizing associations, measurements and context analyzed over the entire federated system;
estimating a likelihood of pathogenicity of the genetic variant based at least on the number of distinct instances of the respective measurement stored within the federated system, wherein estimating the likelihood of pathogenicity of the genetic variant comprises tracking the summary statistics aggregated at the federated layer that relate to a plurality of genetic variants and observed phenotypes and determining a statistical likelihood of pathogenicity of the genetic variant when the genetic variant has been observed a threshold number of times in conjunction with a phenotype; and outputting the likelihood of pathogenicity of the genetic variant single query response to the user.

22. The computer system for sharing data of claim 21, wherein the data structure comprises categories for signs, associations, and evidences of variant data.

23. The computer system for sharing data of claim 21, wherein the summary statistics and the single query response do not include personal information.

24. The computer system for sharing data of claim 21, wherein the federated search is performed in real-time through the federated layer.

25. The computer system for sharing data of claim 21, wherein the summary statistics and the single query response comprise aggregate population statistics.

26. The computer system for sharing data of claim 21, wherein the federated search utilizes one or both of application programming interfaces (APIs) or wrappers so that the summary statistics generated at some or all of the knowledgebases participating in the federated system are in the same data format.

27. The computer system for sharing data of claim 21, wherein the query comprises one or more indications related to a specified measurement corresponding to or indicative of the genetic variant.

28. The computer system for sharing data of claim 21, wherein the federated search comprises a plurality of secondary requests generated for different knowledgebases participating in the federated system.

29. A non-transitory computer-readable medium storing instructions that, when executed by at least one processor of a system, cause one or more computing devices of the system to perform operations comprising:
maintaining or accessing a federated system comprising a plurality of knowledgebases participating in the federated system, wherein the plurality of knowledgebases are connected via by a federated layer;
receiving a query from a user of the federated system, the query comprising at least an indication of a generic variant, wherein the query is configured to execute against a data structure stored on the federated system;
in response to the query, performing a federated search through the federated layer on the plurality of knowledgebases participating in the federated system;
in response to the federated search, receiving summary statistics generated at some or all of the knowledgebases participating in the federated system such that each responsive knowledgebase provides summary statistics responsive to the query, wherein the summary statistics track or count a number of distinct instances of a respective measurement stored within the federated system, wherein the respective measurement corresponds to the genetic variant, and wherein the summary statistics are generated utilizing associations, measurements and context analyzed over the entire federated system;
estimating a likelihood of pathogenicity of the genetic variant based at least on the number of distinct instances of the respective measurement stored within the federated system, wherein estimating the likelihood of pathogenicity of the genetic variant comprises tracking the summary statistics aggregated at the federated layer that relate to a plurality of genetic variants and observed phenotypes and determining a statistical likelihood of pathogenicity of the genetic variant when the genetic variant has been observed a threshold number of times in conjunction with a phenotype; and outputting the likelihood of pathogenicity of the genetic variant.

30. The non-transitory computer-readable medium of claim 29, wherein the data structure comprises categories for signs, associations, and evidences of variant data.

31. The non-transitory computer-readable medium of claim 29, wherein the summary statistics and the single query response do not include personal information.

32. The non-transitory computer-readable medium of claim 29, wherein the federated search is performed in real-time through the federated layer.

33. The non-transitory computer-readable medium of claim 29, wherein the summary statistics and the single query response comprise aggregate population statistics.

34. The non-transitory computer-readable medium of claim 29, wherein the federated search utilizes one or both of application programming interfaces (APIs) or wrappers so that the summary statistics generated at some or all of the knowledgebases participating in the federated system are in the same data format.

35. The non-transitory computer-readable medium of claim 29, wherein the query comprises one or more indications related to a specified measurement corresponding to or indicative of the genetic variant.

36. The non-transitory computer-readable medium of claim 29, wherein the federated search comprises a plurality of secondary requests generated for different knowledgebases participating in the federated system.

37. A computer-implemented method for sharing data, comprising:
   maintaining or accessing a federated system comprising a plurality of knowledgebases participating in the federated system, wherein the plurality of knowledgebases are connected via by a federated layer;
   receiving a query from a user of the federated system, the query comprising at least an indication of a generic variant, wherein the query is configured to execute against a data structure stored on the federated system and comprising categories for signs, associations, and evidences of variant data;
   in response to the query, performing a federated search, in real-time, through the federated layer on the plurality of knowledgebases participating in the federated system;
   in response to the federated search, receiving summary statistics generated at some or all of the knowledgebases participating in the federated system such that each responsive knowledgebase provides summary statistics responsive to the query, wherein the summary statistics track or count a number of distinct instances of a respective measurement stored within the federated system, wherein the respective measurement corresponds to the genetic variant, and wherein the summary statistics are generated utilizing associations, measurements and context analyzed over the entire federated system;
   estimating a likelihood of pathogenicity of the genetic variant based at least on the number of distinct instances of the respective measurement stored within the federated system, wherein estimating the likelihood of pathogenicity of the genetic variant comprises tracking the summary statistics aggregated at the federated layer that relate to a plurality of genetic variants and observed phenotypes and determining a statistical likelihood of pathogenicity of the genetic variant when the genetic variant has been observed a threshold number of times in conjunction with a phenotype; and
   outputting the likelihood of pathogenicity of the genetic variant.

38. The computer-implemented method of claim 37, wherein the summary statistics and the single query response comprise aggregate population statistics.

39. The computer-implemented method of claim 37, wherein the federated search utilizes one or both of application programming interfaces (APIs) or wrappers so that the summary statistics generated at some or all of the knowledgebases participating in the federated system are in the same data format.

40. The computer-implemented method of claim 37, wherein the query comprises one or more indications related to a specified measurement corresponding to or indicative of the genetic variant.

41. The computer-implemented method of claim 37, wherein the federated search is performed in real-time through the federated layer.

* * * * *

UNITED STATES PATENT AND TRADEMARK OFFICE
CERTIFICATE OF CORRECTION

PATENT NO. : 11,244,246 B2
APPLICATION NO. : 16/799071
DATED : February 8, 2022
INVENTOR(S) : Farh et al.

Page 1 of 1

It is certified that error appears in the above-identified patent and that said Letters Patent is hereby corrected as shown below:

In the Claims

Column 36, Line 2, Claim 21 - please remove -- single query response to the user --

Signed and Sealed this
Twenty-fourth Day of May, 2022

Katherine Kelly Vidal
Director of the United States Patent and Trademark Office